US005928922A

United States Patent [19]

Kivirikko et al.

[11] Patent Number: 5,928,922
[45] Date of Patent: Jul. 27, 1999

[54] α2 SUBUNIT OF PROLYL-4-HYDROXYLASE, NUCLEIC ACID SEQUENCES ENCODING SUCH SUBUNIT AND METHODS FOR PRODUCING THE SAME

[75] Inventors: Kari I Kivirikko, Oulu; Taina Pihlajaniemi, Oulunsalo; Tarja Inkeri Helaakoski, Oulu; Pia Pauliina Annunen, Oulu; Ritva Kaarina Nissi, Oulu; Minna Kristiina Nokelainen, Oulu, all of Finland

[73] Assignees: Academy of Finland, Helsinki, Finland; Fibrogen, Inc., South San Francisco, Calif.

[21] Appl. No.: 08/633,879

[22] Filed: Apr. 10, 1996

[51] Int. Cl.$^6$ .......................... C12N 15/53; C12N 15/12; C12N 15/63; C12N 5/10

[52] U.S. Cl. ................... 435/189; 435/69.1; 435/71.1; 435/252.3; 435/325; 435/320.1; 530/356; 536/23.2

[58] Field of Search .................. 435/69.1, 71.1, 435/68.1, 189, 325, 320.1, 252.3; 530/356; 536/23.2

[56] References Cited

PUBLICATIONS

Bassuk et al., 1989, "Prolyl–hydroxylase: Molecular Cloning and the Primary Structure of the α Subunit from Chicken Embryo", *Proc. Natl. Acad. Sci. U.S.A.* 86:7382–886.
Caruthers et al., 1980, "New Chemical Methods for Synthesizing Polynucleotides", *Nucleic Acids Res. Symp. Ser.* 7:215–233.
Cheng et al., 1987, "The Nucleotide Sequence of a Human Cellular Thyroid Hormone Binding Protein Present in Endoplasmic Reticulum", *J. Biol. Chem.* 262:11221–27.
Chow et al., 1981, "Synthesis of Oligodeoxyribonucleotides on Silica Gel Support", *Nucleic Acids Res.* 9:2807–2817.
Crea and Horn, 1980, "Synthesis of Oligonucleotides on Cellulose by a Phosphotriester Method", *Nucleic Acids Res.* 9:2331.
Freedman et al., 1994, "Protein Disulphide Isomerase: Building Bridges in Protein Folding", *Trends Biochem. Sci* 19:331–336.
Heinegård and Oldberg, 1989, "Structure and Biology of Cartilage and Bone Matrix Noncollagenous Macromolecules", *FASEB J.* 3:2042–2051.
Helaakoski et al., 1989, "Molecular Cloning of the α–subunit of human prolyl 4–hydroxylase: The Complete cDNA–derived Amino Acid Sequence and Evidence for Alternative Splicing of RNA Transcripts", *Proc. Natl. Acad. Sci. U.S.A.* 86:4392–96.
Helaakoski et al., 1994, "Structure and Expression of the Human Gene for the αSubunit of Prolyl 4–Hydroxylase", *J. Biol. Chem.* 269:27874–854.
Helaakoski et al., 1995, "Cloning, Baculovirus Expression, and Characterization of a Second Mouse Prolyl 4–Hydroxylase α–subunit Isoform: Formation of an $\alpha_2\beta_2$ Tetramer with the Protein Disulfide–isomerase/β subunit", *Proc. Natl. Acad. Sci. U.S.A.* 92:4427–4431.

John, et al., 1993, "Cell–free Synthesis and Assembly of Prolyl 4–hydroxylase: The Role of the β–subunit (PDI) in Preventing Misfolding and Aggregation of the α–subunit", *EMBO J.* 12:1587–1595.
Kivirriko and Myllya, 1982, "Posttransitional Enzymes in the Biosynthesis of Collagen: Intracellular Enzymes", *Methods. Enzymol.* 82:245–304.
Kivirikko et al., 1989, "Protein Hydroxylation: Prolyl 4–hydroxylase, an Enzyme with Four Cosubstrates and a Multifunctional Subunit", *FASEB J.* 3:1609–1671.
Kivirikko et al., 1990, "Molecular Biology of Prolyl 4–hydroxylase", *Ann. N.Y. Acad. Sci.* 580:132–142.
M.J.C. (CRC, Boca Raton, FL) pp. 1–51.
Koivu et al., 1987, "A Single Polypeptide Acts Both as the βSubunit of Prolyl 4–hydroxylase and as a Protein Disulfide–isomerase", *J. Biol. Chem.* 262:6447–49.
MacNeil et al., 1993, "Isolation of a cDNA Encoding Thymic Shared Antigen–1", *J. Immunol.* 151:6913–23.
Matteucci and Caruthers, 1980, "The Synthesis of Oligodeoxypyrimidines on a Polymer Support", *Tetrahedron Letters* 21:719–722.
Mayne et al., 1993, "Cartilage Degradation: Basic and Clinical Aspects," (Woessner, J.F. and Howell, D.S., eds.) Marcel Dekker, Inc. New York pp. 81–108.
Myllyla et al., 1977, "Mechanism of the Prolyl Hydroxylase Reaction", *Eur. J. Biochem.* 80:349–357.
Myllyla et al., 1992, "Modification of Vertebrate and Algal Prolyl 4–hydroxylases and Vertebrate Lysyl Hydroxylase by Diethyl Pyrocarbonate", *Biochem. J.* 286:923–927.
Noiva et al., 1991, "Peptide Binding by Protein Disulfide Isomerase a Resident Protein of the Endoplasmic Reticulum Lumen", *J. Biol. Chem.* 266:19645–649.
Noiva and Lennarz, 1992, "Protein Disulfide Isomerase", *J. Biol. Chem.* 267:3553–3556.
Noiva et al., 1993, "Peptide Binding to Protein Disulfide Isomerase Occurs at a Site Distinct from the Active Sites", *J. Biol. Chem.* 268:19210–217.
Pihlajaniemi et al., 1987, "Molecular Cloning of the β–subunit of Human Prolyl 4–hydroxylase. This Subunit and Protein Disulphide Isomerase are Products of the Same Gene", *EMBO J.* 6:643–649.
Veijola et al., 1994, "Cloning, Baculovirus Expression, and Characterization of the α Subunit of Prolyl 4–hydroxylase from the Nematode *Caenorhabditis elegans*", *J. Biol. Chem.* 269::26746–753.
von Hejne, G., 1986, "A New Method for Predicting Signal Sequence Cleavage Sites", *Nucleic Acids Res.* 14:4683–4690.
Wetterau et al., 1990, "Protein Disulfide Isomerase is a Component of the Microsomal Triglyceride Transfer Protein Complex", *J. Biol. Chem.* 265:9800–9807.
Auffray et al (1995) C.R. Acad Sci III, Sci. Vie 318:263–272 "Image:molecular integration of the analysis of the human genome . . . ", Genbank Seg. F10703.
Hillier et al (1995) "The Washu–Merck EST Project", Genbank T76935.

*Primary Examiner*—Rebecca E. Prouty
*Attorney, Agent, or Firm*—Pennie & Edmonds LLP

[57] ABSTRACT

The present invention relates to novel isoforms of the α subunit of prolyl-4-hydroxylase, polynucleotide sequences encoding these novel proteins, and methods for making such proteins.

9 Claims, 12 Drawing Sheets

FIG. 1A

```
   1 GCAGTTTCAGAGACCGGTGGCGATTGGCTGACTGATTCAACAAATAGAGCATTCTCTGCCTGGAGACTTTCAAGGACTGAGGCAGGAAGGAAGACTCAGAAAGTTCAGGTCCAG

121 AGCATCAGCAAGGTACTGCCCTTTCCAGTTATGAAGCTCCAGGTGTTGGTGTTGCTGATGTCCAGGTGTTCCTGAGCTGGGTGTCCTGAGCTGGTGTCCTGAGCAGAATTCTTCACTTCCATTGGG
 -19                               M  K  L  Q  V  L  V  L  L  M  S  W  F  G  V  L  S  W  V  Q  A  E  F  F  T  S  I  G
                                                                                                  Y
 241 CACATGACCGATCTGATTTACGCAGAAGGACCTGGTACAGTCTCTGAAGGAGTACATCCTTGTGGAGGAAGCCAAGCTCGCCAAGATTAAGAGCTGGGCCAAGATGGAAGCCCTG
  12  H  M  T  D  L  I  Y  A  E  K  D  L  V  Q  S  L  K  E  Y  I  L  V  E  E  A  K  L  A  K  I  K  S  W  A  S  K  M  E  A  L

361 ACCAGCAGATCAGCTGCCGACCCCGAGGGCTACCTGGCTCATCCTGTGAATGCCTACAAGCTGGTGAAGCGGTTGAACACAGACTGGCCTGCACTGGGAGACTTGTCCTTCAGGATGCT
  52  T  S  R  S  A  A  D  P  E  G  Y  L  A  H  P  V  N  A  Y  K  L  V  K  R  L  N  T  D  W  P  A  L  G  D  L  V  L  Q  D  A

481 TCGGCAGGTTTTGTGCTAACCTCAGTTCAGGGCAATTCTTCCCCACTGATGAGGACGAGTCTGGAGCCCTGATGAGACTTCAGGACGTACAAACTGGATCCGGAC
  92  S  A  G  F  V  A  [N  L  S]  V  Q  R  Q  F  F  P  T  D  E  D  E  S  G  A  A  R  A  L  M  R  L  Q  D  T  Y  K  L  D  P  D

601 ACGATTTCCAGAGGGGAACTTCCAGGCACACAAGTACCCAGCTCAGTTCAGAGGAGCCACTGTTACCAAGTCCCTGGTGCTGCTGAGCTACTGCCACCGTGCTGTGGAA
 132  T  I  S  R  G  E  L  P  G  T  K  Y  Q  A  M  L  S  V  D  D  Ⓕ  F  G  L  G  R  S  A  Y  N  E  G  D  Y  Y  H  T  V  L  W

721 ATGGAGCAGGTACTGAAGCAGCTCGATGCTGGGGAGGAGGCCACTGTTACCAAGTCCCTGGTGCTGCTGAGCTACTGTCTCCAACTGGGTCTCTTCCAACTGGGTGACCTGCACCGTGCTGTGGAA
 172  M  E  Q  V  L  K  Q  L  D  A  G  E  E  A  T  V  T  K  S  L  V  L  D  Y  L  S  Y  A  V  F  Q  L  G  D  L  H  R  A  V  E

841 CTCACCCGCCGCCTGCTCTCTCTTGACCCAAGCCACGAGAGGGCTGGGGGAATCTGGTTGTTGAGAGGAAGAAAGAGGGAAGAAATCACTGTCAAATCAGACAGACGCC
 212  L  T  R  R  L  L  S  L  D  P  S  H  E  R  A  G  G  N  L  R  Y  F  E  R  L  L  E  E  E  R  G  K  S  L  S  [N  Q  T]  D  A

961 GGACTGGCCACCCAGGAAACTTGTACGAGAGGCCCACGGACTACCTGCCTGAGAGGGATGTGTACGAGGAGGGCGTGAAACTGACACCCCGGAGGCAGAAGAAG
 252  G  L  A  T  Q  E  N  L  Y  E  R  P  T  D  Y  L  P  E  R  D  V  Y  E  E  S  L  Ⓡ  R  G  E  G  V  K  L  T  P  R  R  Q  K  K

1081 CTTTTCTGTAGGTACCATCATGGAAACAGAGTGCCACAGCTCCTCATCGCCCCCTTCAAAGAGGAAGACAGTGGGACACCCACATCGTCAGGTACTATGATGTGATGTCCGACGAA
 292  L  F  Ⓒ  R  Y  H  H  G  N  R  V  P  Q  L  L  I  A  P  F  K  E  E  D  S  P  H  I  V  R  Y  Y  D  V  M  S  D  E

1201 GAAATCGAGAGGATCAAGGAGATTGCTAAGCCACCTGTCCTCACTGTTGCGTACTACAGAGTTTCCAAAAGCTCCTGGCTAGAG
 332  E  I  E  R  I  K  E  I  A  K  P  K  L  A  R  A  T  V  R  D  D  P  K  T  G  V  L  T  V  A  S  Y  R  V  S  K  S  S  W  L  E
```

FIG. 1B

```
1321 GAGGATGACGACCCTGTTGTGGCCCGGGTCAACCGGCGATGCAACATATCACCGGGCTAACGGTGAAGACTGCAGAGCTATTGCAGGTCGCAAACTACGGAATGGGGACAGTACGAA
 372  E   D   D   D   P   V   V   A   R   V   N   R   R   M   Q   H   I   T   G   L   T   V   K   T   A   E   L   L   Q   V   A   N   Y   G   M   G   G   Q   Y   E

1441 CCACACTTTGACTTCTCAAGGAGCGATGACGAAGATGCTTTCAAGCGTTTAGGGACTGGGAACCGTGTGGCCACGTTTCTAAACTACATGAGCGATGTCGAAGCTGGTGGTGCCACCGTC
 412  P   H   F   D   F   S   R   S   D   D   E   D   A   F   K   R   L   G   T   G   N   R   V   A   T   F   L   N   Y   M   S   D   V   E   A   G   G   A   T   V

1561 TTTCCTGACTTGGGAGCTGCTATTTGGCCCAAGAAGGGACACAGTCTGTATTCTCGGTACAACCTTCTTCGCAGTGGGGAAGGTGATTATCGACGAGACATGCAGCCTGCCCTGTGCTTGTG
 452  F   P   D   L   G   A   A   I   W   P   K   K   G   T   A   V   F   W   Y   N   L   L   R   S   G   E   G   D   Y   R   T   R   H   A   A   ⓒ   P   V   L   V

1681 GGCTGCAAGTGGGTCTCCAACAAGTGTTCCATGAGCGAGGACAGGAGTTCTTAAGACCTTGTGGAACAACGAAGTTGATTGACGTCCTTTTCTCCGCTCCTCCCGCTCCTGGCCCATAGTC
 492  G   ⓒ   K   W   V   S   N   K   W   F   H   E   R   G   Q   E   F   L   R   P   ⓒ   G   T   T   E   V   D

1801 CAAATCATCTTCAAGTTCAACATGACAGCTTCCTTTTTTATGTCCCAGCTCCGTCTCAGGCAGGTCATTGGAGGAGCCAGTGTTGACTGAATTGAGAGAGTATATCCTGACCCTAGTCCT

1921 GGGTGACCTGGGCCCCAGACTCTGACCAGCTTACACCTGCCCTGCCTCTGGGGGTGTCTTGGCATGGCTGCGGGTAGAGCCAGACTATAGCACCCGGCACGGTCGCTTTGTACCTCAGATA

2041 TTTCAGGTAGAAGATGTCTCAGTGAAACCAAAGTTCTGATGTGTTTTATCACATTTCTATTTGTTGTGGCTTTAACCAAAAAATAAAAATGTTCCTGCCAAAAAAA

2161 AAAAAAAA
```

FIG. 2A

```
              9        18        27        36        45        54        63        72
5' GGAACAGGGGAACTGTAGGGGATAGCTGTCCACGGACGCTGTCTACAAGACCCTGGAGTGAGATAACGTGCC 81        90        99       108       117       126       135       144
   TGGTACTGTGCCCTGCATGTGTAAGATGCCCAGTTGACCTTCGCAGCAGGAGCCTGGATCAGGCACTTCCTG 153       162       171       180       189       198       207       216
   CCTCAGGTATTGCTCGACAGCCCAGACACTTCCCTCTGTGACCATGAAACTCTGGGTGTCTGCATTGCTGAT
                                                   MetLysLeuTrpValSerAlaLeuLeuMet
                                                      exon②   exon③
            225       234       243       252       261       270       279       288
   GGCCTGGTTTGGTGTCCTGAGCTGTGTGCAGGCCGAATTCTTCACCTCTATTGGGCACATGACTGACCTGAT
   AlaTrpPheGlyValLeuSerCysValGlnAlaGluPhePheThrSerIleGlyHisMetThrAspLeuIle 297       306       315       324       333       342       351       360
   TTATGCAGAGAAAGAGCTGGTGCAGTCTCTGAAAGAGTACATCCTTGTGGAGGAAGCCAAGCTTTCCAAGAT
   TyrAlaGluLysGluLeuValGlnSerLeuLysGluTyrIleLeuValGluGluAlaLysLeuSerLysIle
               exon④
            369       378       387       396       405       414       423       432
   TAAGAGCTGGGCCAACAAAATGGAAGCCTTGACTAGCAAGTCAGCTGCTGATGCTGAGGGCTACCTGGCTCA
   LysSerTrpAlaAsnLysMetGluAlaLeuThrSerLysSerAlaAlaAspAlaGluGlyTyrLeuAlaHis 441       450       459       468       477       486       495       504
   CCCTGTGAATGCCTACAAACTGGTGAAGCGGCTAAACACAGACTGGCCTGCGCTGGAGGACCTTGTCCTGCA
   ProValAsnAlaTyrLysLeuValLysArgLeuAsnThrAspTrpProAlaLeuGluAspLeuValLeuGln
                            exon⑤
            513       522       531       540       549       558       567       576
   GGACTCAGCTGCAGGTTTTATCGCCAACCTCTCTGTGCAGCGGCAGTTCTTCCCCACTGATGAGGACGAGAT
   AspSerAlaAlaGlyPheIleAlaAsnLeuSerValGlnArgGlnPhePheProThrAspGluAspGluIle 585       594       603       612       621       630       639       648
   AGGAGCTGCCAAAGCCCTGATGAGACTTCAGGACACATACAGGCTGGACCCAGGCACAATTTCCAGAGGGGA
   GlyAlaAlaLysAlaLeuMetArgLeuGlnAspThrTyrArgLeuAspProGlyThrIleSerArgGlyGlu
                       exon⑥
            657       666       675       684       693       702       711       720
   ACTTCCAGGAACCAAGTACCAGGCAATGCTGAGTGTGGATGACTGCTTTGGGATGGGCCGCTCGGCCTACAA
   LeuProGlyThrLysTyrGlnAlaMetLeuSerValAspAspCysPheGlyMetGlyArgSerAlaTyrAsn 729       738       747       756       765       774       783       792
   TGAAGGGGACTATTATCATACGGTGTTGTGGATGGAGCAGGTGCTAAAGCAGCTTGATGCCGGGGAGGAGGC
   GluGlyAspTyrTyrHisThrValLeuTrpMetGluGlnValLeuLysGlnLeuAspAlaGlyGluGluAla 801       810       819       828       837       846       855       864
   CACCACAACCAAGTCACAGGTGCTGGACTACCTACGCTATGCTGTCTTCCAGTTGGGTGATCTGCACCGTGC
   ThrThrThrLysSerGlnValLeuAspTyrLeuArgTyrAlaValPheGlnLeuGlyAspLeuHisArgAla
                                        exon⑦
            873       882       891       900       909       918       927       936
   CCTGGAGCTCACCCGCCGCCTGCTCTCCCTTGACCCAAGCCACGAACGAGCTGGAGGGAATCTGCGGTACTT
   LeuGluLeuThrArgArgLeuLeuSerLeuAspProSerHisGluArgAlaGlyGlyAsnLeuArgTyrPhe 945       954       963       972       981       990       999      1008
   TGAGCAGTTATTGGAGGAAGAGAGAGAGAAAAAACGTTAACAAATCAGACAGAAGCTGAGCTAGCAACCCAGA
   GluGlnLeuLeuGluGluGluArgGluLysThrLeuThrAsnGlnThrGluAlaGluLeuAlaThrProGlu
```

FIG. 2B

```
              1017      1026      1035      1044      1053      1062      1071      1080
          AGGCATCTATGAGAGGCCTGTGGACTACCTGCCTGAGAGGGATGTTTACGAGAGCCTCTGTCGTGGGGAGGG
             GlyIleTyrGluArgProValAspTyrLeuProGluArgAspValTyrGluSerLeuCysArgGlyGluGly
                              exon ⑧
              1089      1098      1107      1116      1125      1134      1143      1152
          TGTCAAACTGACACCCCGTAGACAGAAGAGGCTTTTCTGTAGGTACCACCATGGCAACAGGGCCCCACAGCT
             ValLysLeuThrProArgArgGlnLysArgLeuPheCysArgTyrHisHisGlyAsnArgAlaProGlnLeu 1161      1170      1179      1188      1197      1206      1215      1224
          GCTCATTGCCCCCTTCAAAGAGGAGGACGAGTGGGACAGCCCGCACATCGTCAGGTACTACGATGTCATGTC
             LeuIleAlaProPheLysGluGluAspGluTrpAspSerProHisIleValArgTyrTyrAspValMetSer
                                                                 exon ⑨/⑩
              1233      1242      1251      1260      1269      1278      1287      1296
          TGATGAGGAAATCGAGAGGATCAAGGAGATCGCAAAACCTAAACTTGCACGAGCCACCGTTCGTGATCCCAA
             AspGluGluIleGluArgIleLysGluIleAlaLysProLysLeuAlaArgAlaThrValArgAspProLys
                                                              exon ⑪
              1305      1314      1323      1332      1341      1350      1359      1368
          GACAGGAGTCCTCACTGTCGCCAGCTACCGGGTTTCCAAAAGCTCCTGGCTAGAGGAAGATGATGACCCTGT
             ThrGlyValLeuThrValAlaSerTyrArgValSerLysSerSerTrpLeuGluGluAspAspAspProVal
                                                                              exon ⑫
              1377      1386      1395      1404      1413      1422      1431      1440
          TGTGGCCCGAGTAAATCGTCGGATGCAGCATATCACAGGGTTAACAGTAAAGACTGCAGAATTGTTACAGGT
             ValAlaArgValAsnArgArgMetGlnHisIleThrGlyLeuThrValLysThrAlaGluLeuLeuGlnVal
                                                             exon ⑬
              1449      1458      1467      1476      1485      1494      1503      1512
          TGCAAATTATGGAGTGGGAGGACAGTATGAACCGCACTTCGACTTCTCTAGGAATGATGAGCGAGATACTTT
             AlaAsnTyrGlyValGlyGlyGlnTyrGluProHisPheAspPheSerArgAsnAspGluArgAspThrPhe
                                                                 exon ⑭
              1521      1530      1539      1548      1557      1566      1575      1584
          CAAGCATTTAGGGACGGGGAATCGTGTGGCTACTTTCTTAAACTACATGAGTGATGTAGAAGCTGGTGGTGC
             LysHisLeuGlyThrGlyAsnArgValAlaThrPheLeuAsnTyrMetSerAspValGluAlaGlyGlyAla
                                                           exon ⑮
              1593      1602      1611      1620      1629      1638      1647      1656
          CACCGTCTTCCCTGATCTGGGGGCTGCAATTTGGCCTAAGAAGGGTACAGCTGTGTTCTGGTACAACCTCTT
             ThrValPheProAspLeuGlyAlaAlaIleTrpProLysLysGlyThrAlaValPheTrpTyrAsnLeuLeu
                                                                             exon ⑯
              1665      1674      1683      1692      1701      1710      1719      1728
          GCGGAGCGGGGAAGGTGACTACCGAACAAGACATGCTGCCTGCCCTGTGCTTGTGGGCTGCAAGTGGGTCTC
             ArgSerGlyGluGlyAspTyrArgThrArgHisAlaAlaCysProValLeuValGlyCysLysTrpValSer 1737      1746      1755      1764      1773      1782      1791      1800
          CAATAAGTGGTTCCATGAACGAGGACAGGAGTTCTTGAGACCTTGTGGATCAACAGAAGTTGACTGACATCC
             AsnLysTrpPheHisGluArgGlyGlnGluPheLeuArgProCysGlySerThrGluValAsp 1809      1818      1827      1836      1845      1854      1863      1872
          TTTTCTGTCCTTCCCCTTCCTGGTCCTTCAGCCCATGTCAACGTGACAGACACCTTTGTATGTTCCTTGTAT 1881      1890      1899      1908      1917      1926      1935      1944
          GTTCCTATCAGGCTGATTTTTGGAGAAATGAATGTTTGTCTGGAGCAGAGGGAGACCATACTAGGGCGACTC
```

FIG. 2C

```
      1953      1962      1971      1980      1989      1998      2007      2016
CTGTGTGACTGAAGTCCCAGCCCTTCCATTCAGCCTGTGCCATCCCTGGCCCCAAGGCTAGGATCAAAGTGG 2025      2034      2043      2052      2061      2070      2079      2088
CTGCAGCAGAGTTAGCTGTCTAGCGCCTAGCAAGGTGCCTTTGTACCTCAGGTGTTTTAGGTGTGAGATGTT 2097      2106      2115      2124      2133      2142      2151      2160
TCAGTGAACCAAAGTTCTGATACCTTGTTTACATGTTTGTTTTTATGGCATTTCTATCTATTGTGGCTTTAC 2169      2178      2187
CAAAAAATAAAATGTCCCTACCAGAAGCCTTAAA
```

FIG. 3

```
       10        20        30        40        50        60
5'GGGGAAGGAACACTGTAGGGGATAGCTGTCCACGGACGCTGTCTACAAGACCCTGGAGTG 70        80        90       100       110       120
AGATAACGTGCCTGGTACTGTGCCCTGCATGTGTAAGATGCCCAGTTGACCTTCGCAGCA 130       140       150       160       170       180
GGAGCCTGGATCAGGCACTTCCTGCCTCAGGTATTGCTGGACAGCCCAGACACTTCCCTC 190       200       210       220       230       240
TGTGACCATGAAACTCTGGGTGTCTGCATTGCTGATGGCCTGGTTTGGTGTCCTGAGCTG
         M  K  L  W  V  S  A  L  L  M  A  W  F  G  V  L  S  C
                                    exon②    intron
      250       260       270       280       290       300
TGTGCAGGCCGAATTCTTCACCTCTATTGGTACGTGCCAACAGGACTGTCGTCTCCCTGA
 V  Q  A  E  F  F  T  S  I  G 310       320       330       340       350       360
CACCTTGGCTCACATGCCACGGATGTCTCTGGCTGCAGCTGTTCTCATTTAGAGTGGGAT

370
AGCCTTAACATACGG 3'
```

FIG. 4

```
 exon③
       10        20        30        40        50        60
5'GGCACATGACTGACCTGATTTATGCAGAGAAAGAGCTGGTGCAGTCTCTGAAAGAGTACA
   H  M  T  D  L  I  Y  A  E  K  E  L  V  Q  S  L  K  E  Y  I
                                     exon③     intron
       70        80        90       100       110       120
TCCTTGTGGAGGAAGCCAAGCTTTCCAAGATTAAGAGGTGTCCTAAGTCCCCATACCATC
  L  V  E  E  A  K  L  S  K  I  K 130       140       150       160       170       180
CTTAGTTGGCCTTCCTTCCCTTCTGCCCTCAAGGAACAAGGAAGCCATCAGGGTGCCTAT 190       200
AACATTAAACCTTTGAGAGG 3'
```

FIG. 5

```
         10        20        30        40        50        60
5'GGGAATTCTCACTAGAAAATTGTCACAGGTCAAGACCTATGTGGGTGGACGCATTAGTCT
                    intron       exon④
         70        80        90       100       110       120
  TCCTTTTCCTCTGGTTCCACAG CTGGGCCAACAAAATGGAAGCCTTGACTAGCAAGTCAG
                         S  W  A  N  K  M  E  A  L  T  S  K  S  A 130       140       150       160       170       180
  CTGCTGATGCTGAGGGCTACCTGGCTCACCCTGTGAATGCCTACAAACTGGTGAAGCGGC
   A  D  A  E  G  Y  L  A  H  P  V  N  A  Y  K  L  V  K  R  L
                                              exon④       intron
        190       200       210       220       230       240
  TAAACACAGACTGGCCTGCGCTGGAGGACCTTGTCCTGCAGGACTCAGCTGCAG GTGAGG
   N  T  D  W  P  A  L  E  D  L  V  L  Q  D  S  A  A 250       260       270       280       290       300
  GACGGTGACGAGGTGCTTGAGTGAGCCCATATGTTTGTGTGCTCATGCCTGGGTTGTTGT 310       320       330
  GTCTGAGCCTGTCTTGGGTCTGGGTGTTGG 3'
```

FIG. 6

```
         10        20        30        40        50        60
5'GAGACCCTCTTTGTGGCTGCCTCTCTGGGTCCCAAGTGGAATTCTGCCCCTGGATCAAGG
                              intron       exon⑤
         70        80        90       100       110       120
  GTAATCTCTTGTTCTGACTCTTCATTTGGAAG GTTTTATCGCCAACCTCTCTGTGCAGCG
                                    G  F  I  A  N  L  S  V  Q  R 130       140       150       160       170       180
  GCAGTTCTTCCCCACTGATGAGGACGAGATAGGAGCTGCCAAAGCCCTGATGAGACTTCA
   Q  F  F  P  T  D  E  D  E  I  G  A  A  K  A  L  M  R  L  Q
                                              exon⑤       intron
        190       200       210       220       230       240
  GGACACATACAGGCTGGACCCAGGCACAATTTCCAGAGGGGAACTTCCAG TAACTCACC
   D  T  Y  R  L  D  P  G  T  I  S  R  G  E  L  P  G 250       260       270       280       290       300
  ACTCCAGGCGTTGCTGTCCCGCATGTGTCTCTTTAGTGGCGGGACAGGTTGGAGCCACCA 310       320       330       340       350       360
  CCAACTTGTGGCCTTTAACCTCGGGTGCACCTCTCTCTTGGCACACCAGTTGTGCTGGAC

TCCTCTCCA 3'
```

FIG. 7

```
intron    exon 6
          10         20         30         40         50         60
     5' GAACCAAGTACCAGGCAATGCTGAGTGTGGATGACTGCTTTGGGATGGGCCGCTCGGCCT
         T  K  Y  Q  A  M  L  S  V  D  D  C  F  G  M  G  R  S  A  Y 70         80         90        100        110        120
        ACAATGAAGGGGACTATTATCATACGGTGTTGTGGATGGAGCAGGTGCTAAAGCAGCTTG
         N  E  G  D  Y  Y  H  T  V  L  W  M  E  Q  V  L  K  Q  L  D 130        140        150        160        170        180
        ATGCCGGGGAGGAGGCCACCACAACCAAGTCACAGGTGCTGGACTACCTACGCTATGCTG
         A  G  E  E  A  T  T  T  K  S  Q  V  L  D  Y  L  R  Y  A  V
                                                      exon 6    intron
         190        200        210        220        230        240
        TCTTCCAGTTGGGTGATCTGCACCGTGCCCTGGAGCTCACCCGCCGCCTGCTCTCCCTTG
         F  Q  L  G  D  L  H  R  A  L  E  L  T  R  R  L  L  S  L 250        260        270        280        290        300
        GTAAGGAGATTCTAGGGGAAGGTAAGATGGGAATGGAGAGTGGCAGAGGAACTGCACTGT

GCCTGGCAC 3'
```

FIG. 8

```
              10         20         30         40         50         60
5'TTAGATGCTGTGAAGGATGATGCACGCATGCAGGTGAGCTGCTGGGAGAGAAACCCTTAC 70         80         90        100        110        120
  TACTCTGGTTAGATGCTGTGAAGGATGAATGCAGCATGCAGGTGAGCTGCTCCCAGAGAA 130        140        150        160        170        180
  ACCCTTACAGATAATTTCTCTAAATGACCTAACAGATGTTTGTGGTTTCCTTTTCCTTCT
                              intron    exon⑦
             190        200        210        220        230        240
  CATTCCTTGCATTTTCTG ACCCAAGCCACGAACGAGCTGGAGGGAATCTGCGGTACTTTG
                      D  P  S  H  E  R  A  G  G  N  L  R  Y  F  E 250        260        270        280        290        300
  AGCAGTTATTGGAGGAAGAGAGAGAAAAAACGTTAACAAATCAGACAGAAGCTGAGCTAG
   Q  L  L  E  E  E  R  E  K  T  L  T  N  Q  T  E  A  E  L  A 310        320        330        340        350        360
  CAACCCCAGAAGGCATCTATGAGAGGCCTGTGGACTACCTGCCTGAGAGGGATGTTTACG
   T  P  E  G  I  Y  E  R  P  V  D  Y  L  P  E  R  D  V  Y  E
                                         exon⑦    intron
             370        380        390        400        410        420
  AGAGCCTCTGTCGTGGGGAGGGTGTCAAACTG GTGAGATGTGTGAGGGGGCTAGGGTGCC
   S  L  C  R  G  E  G  V  K  L 430        440        450        460        470        480
  AAAGCTGTGGACCTGGACTCTGGCCTCTGGGCAGGCAGATTTGGGGAAGGTGTTCTTTAT 490        500
  TCTGAGGTACTTTTCACGTTTCCCGTTTT 3'
```

FIG. 9A

```
       10         20         30         40         50         60
5'TGGCCATGAGGTGAGTCCAGTGTCTGCAGACAGCCAGACTGGGACCGAGGATTAGGACTC
                                    intron    exon ⑧
       70         80         90       100        110        120
ACTCAGCTCAGGGCCTGTTACTCTGTGCTTTC(AG)(C)ACACCCCGTAGACAGAAGAGGCTT
                                       T  P  R  R  Q  K  R  L 130        140        150        160        170        180
TTCTGTAGGTACCACCATGGCAACAGGGCCCCACAGCTGCTCATTGCCCCCTTCAAAGAG
 F  C  R  Y  H  H  G  N  R  A  P  Q  L  L  I  A  P  F  K  E 190        200        210        220        230        240
GAGGACGAGTGGGACAGCCCGCACATCGTCAGGTACTACGATGTCATGTCTGATGAGGAA
 E  D  E  W  D  S  P  H  I  V  R  Y  Y  D  V  M  S  D  E  E
                                exon ⑧     intron
      250        260        270        280        290        300
ATCGAGAGGATCAAGGAGATCGCAAAACCTAAA(G)(T)AGGTGTACAGTGAGGCCTTCTCGG
 I  E  R  I  K  E  I  A  K  P  K 310        320        330        340        350        360
GTCACTGAAGGGGGAAGGTCTTTTTCTCATCCCCTAGCACTATGGGTGGTTAGAGTTTGC 370        380        390        400        410        420
CCATCCTAGCCACCCTTTATCCATATCTAGCATAGGGCCTACCTGGAGGGATACAGAGAT 430        440        450        460        470        480
GCTTCAGACTCAGCCTGACCTTGTGAGGTTCATGTGCCAGTGGAAGGAAGGAACAGGGTA 490        500        510        520        530        540
ACCAATGTGGACAGCCAAGTGCTATCATACAAGGTCACGTCCTGGGAACAGGGCTGGGAA 550        560        570        580        590        600
CAGGGCAGGTCTACACTGGTGTGTCAGTTCACCTGGTTGGGAGACTGGTGCGTGGGTGAG 610        620        630        640        650        660
TTTTTTGGAAATGTTCCATAGGATGCTATGAAGCTGGGTCCTGTGGAGCTCCTGAGTAGG 670        680        690        700        710        720
ACTGTAAATGAGGTGAATGACTTAGAGGAGAATGTATATCTTTTATAATATTTGGGTCTC 730        740        750        760        770        780
TCATCCAAGGGCATGACAGGTCTCTCCATATCTTTTAAGTTTTCTTCATATAAGCCTTG 790        800        810        820        830        840
AACATGTCTTAAGTTTATTCCTTGGTACTTTCTTTGTTACTGTTAATTTACTTTATTTCT 850        860        870        880        890        900
TCATTATTATTTTAACTGGTTACATTATTTATTAGTTTACTATTATATGCCAAACTATTG
```

FIG. 9B

```
          910       920       930       940       950       960
ATTTTACAAATACATTTCATAGTAAGAGCTAATGTTTACTGAATTCTTAACTGTGGCAGG 970       980       990      1000      1010      1020
AAACTTCTAAGTGCTTAACATATATATTAAGTGTTATGTCACAGTTATGAACAGCTGCTC 1030      1040      1050      1060      1070      1080
AGAATGATGTCACTGTCTCTGTTTTACCTATGAAAAAGCAAACTCATACAGATTGCAGCT 1090      1100      1110      1120      1130      1140
AGTGGTTGAATTTACTTATTTGTTTTTTGGTTTTACGTGATTTCTCTTTGGTTGGGTGGA 1150      1160      1170      1180      1190      1200
TAGCATTAACACCTGGAAATAAGGAAAATTTTATTTTCTCCTGATACTTGTAGTTCCTTT 1210      1220      1230      1240      1250      1260
GTTTTTATAACCTTATTGAATTGCCCAGAACTTCTAGAGCATAATTACGTAGAATAGGCA 1270      1280      1290      1300      1310      1320
TCCTTGTCTCATTCCTGAATTTCCTGGGAAATTCCTATGGTATTTACTGCTAAGAATGCA 1330      1340      1350      1360      1370      1380
GTTGGCTGTTGGTTTTGTATATATGCCAAAATTATTCTTCTGTTTCTAGTTCATAAAAGA 1390      1400      1410      1420      1430      1440
TTTGTTCCCCATTTGACATCTTTCAAAGAGACCTATTTGCTGCCATATCCCATCACTGAT 1450      1460      1470      1480      1490      1500
GATTGGGAGGGAGGATTTAGCTCGATTCTCTATGCTCTGCTCCTAATAGAATTGTAGGGG 1510      1520      1530      1540      1550      1560
CCGAGGTGACCAGGAGGCCCGACACTCATGGAGAGACCTGAAATAGGTTCCTATCCTGGC 1570      1580      1590      1600      1610      1620
CCCTGGACCTCATCTTGGAACAGCTTTGGCTTGAGGTACTAGGACATCTAGGGCTTTGAG 1630      1640      1650      1660      1670      1680
TCAGTGGTTGGCATCATCGATGTGGCTGAGGAAGGGGGCTAGCCAGATATATGGAGAATG 1690      1700      1710      1720      1730      1740
GGGACTAGGACTCCCCTTTCTACTCAGCTCCAGAGTCCTCCAGGAAAGAAAACTACTTTG
                    Intro 8/8 (1760) ⟶
         1750      1760      1770      1780      1790      1800
TTGGTTGTGCCAGGTTTCCTGAGAGATTCCTTACCCGTTCTTTCAGTTCCAGACACTGAG
              Intro 8/8 (1810) ⟶
         1810      1820      1830      1840      1850      1860
AACATTTCTCTGTGCATGTGTGCATATGTGTACACATGTGTGTGGCTGGCCACAGGGTAG
```

FIG. 9C

```
         1870       1880       1890       1900       1910       1920
TGTTAGGAAAAGATATATTTGAATAGAAGCCATGCAAAGAGCCAAACAAGGTTGGCAAAC 1930       1940       1950       1960       1970       1980
ATGTTTGGCTCTTAACATGGCTTCTATTCAAAGATAAGCTGACCCCTCCTTTCCGGAGAC

Intro 8/8 1990 →
         1990       2000       2010       2020       2030       2040
TGTGAGGGACAGATGCTATTCTGGCTTTCAAGTAGAGCCAATGAGCTTAACTTGGCCTGT Intro 8/8 2070 →
         2050       2060       2070       2080       2090       2100
GGGGAATGCCTGGCAGCTGTCTGTGGGGTCTCTGGCCTGCTTTCAAAATAGCCCTGTCG 2110       2120
TTAAAATGGGACAGCATCAGTGC 3'
```

α2 SUBUNIT OF PROLYL-4-HYDROXYLASE, NUCLEIC ACID SEQUENCES ENCODING SUCH SUBUNIT AND METHODS FOR PRODUCING THE SAME

1. INTRODUCTION

The present invention relates to the identity and characterization of novel α subunits of prolyl-4-hydroxylase, variants thereof, polynucleotide sequences which encode the novel α2 subunits of prolyl-4-hydroxylase, and methods for using and making such novel polynucleotides and polypeptides. The present invention also relates to the recombinant production of active: (1) prolyl-4-hydroxylase, or variants thereof, and (2) collagen, comprising the use of the novel human α subunit of prolyl-4-hydroxylase of the present invention.

The present invention more specifically relates to polynucleotides encoding a novel isoform of the α subunit of prolyl-4-hydroxylase, designated the "α2 subunit," and derivatives thereof, methods for producing such isoforms or related derivatives and the use of these proteins and polynucleotides in the production of recombinant collagen.

2. BACKGROUND

General Information Regarding Collagen.

Collagen fibrils, proteoglycan aggregates and glycoproteins are critical components of the cartilage extracellular matrix that, collectively, resist compression and the tensile and shear forces that are generated during articulation. Heinegård and Oldberg (1989) *FASEB J.* 3:2042–2051; Mayne and Brewton, *Cartilage Degradation: Basic and Clinical Aspects* (Woessner, J. F. and Howell, D. S., eds.) Marcel Dekker, Inc., New York, pp. 81–108 (1993). Mutations in cartilage matrix genes or the genes which encode the enzymes that affect the biosynthesis, assembly or interactions between these various matrix components may contribute to degradation of the cartilage matrix and the loss of normal cartilage function.

The Role Of Prolyl-4-Hydroxylase In The Production Of Collagen.

Prolyl-4-hydroxylase plays a crucial role in the synthesis of all collagens. Specifically, the enzyme catalyzes the formation of 4-hydroxyproline in collagens and related proteins by the hydroxylation of proline residues in -Xaa-Pro-Bly-sequences. These 4-hydroxyproline residues are essential for the folding of newly synthesized collagen polypeptide chains into triple-helical molecules.

The vertebrate prolyl-4-hydroxylase is an $\alpha_2\beta_2$ tetramer in which the α subunits contribute to most parts of the catalytic sites. See, Kivirikko, et al., (1989) *FASEB J.* 3, 1609–1617; Kivirikko, et al., (1990) *Ann. N.Y. Acad. Sci.* 580, 132–142; Kivirikko, et al., (1992), *Post Translational Modifications of Proteins*, eds. Harding, J. J. & Crabbe, M. J. C. (CRC, Boca Raton, Fla.), pp. 1–51. The β subunit has been cloned from many sources (id.; see also, Noiva and Lennatz, (1992) *J. Biol. Chem.* 267:6447–49; Freedman, et al., (1994) *Trends Biochem. Sci.* 19:331–336) and has been found to be a highly unusual multifunctional polypeptide that is identical to the enzyme protein disulfide-isomerase (Pihlajaniemi, et al. (1987) *EMBO J.* 6:643–649; Kojvu, et al., (1987) *J. Biol. Chem.* 262:6447–49), a cellular thyroid hormone-binding protein (Cheng, et al. (1987) *J. Biol. Chem.* 262:11221–27), the smaller subunit of the microsomal triacylglycerol transfer protein (Wetterau, et al., (1990) *J. Biol. Chem.* 265:9800–07), and an endoplasmic reticulum luminal polypeptide which uniquely binds to various peptides (Freedman, supra; Noiva, et al. (1991) *J. Biol. Chem.* 266:19645–649; Noiva, et al. (1993) *J. Biol. Chem.* 268:19210–217).

A catalytically important α subunit, designated the α1 subunit, has been cloned from human (Helaakoski, et al. (1989) *Proc. Natl. Acad. Sci. (USA)* 86:4392–96), chicken (Bassuk, et al. (1989) *Proc. Natl. Acad. Sci. (USA)* 86:7382–886) and *Caenorhabditis elegans* (Veijola, et al. (1994) *J. Biol. Chem.* 269:26746–753), and its RNA transcripts have been shown to undergo alternative splicing involving sequences encoded by two consecutive, homologous 71-bp exons (Helaakoski, supra; Helaakoski, et al. (1994) *J. Biol. Chem.* 269:27847–854). A second a subunit, designated the α2 subunit has been previously obtained from mouse. Helaakoski, et al. (1995) *Proc. Natl.Acad.Sci. (USA)* 92:4427–4431.

3. SUMMARY OF THE INVENTION

The present invention is directed to the cloning and characterization of human α-subunit isoforms of prolyl-4-hydroxylase. More specifically, the present invention relates to human subunit isoforms of the a subunit of prolyl-4-hydroxylase designated the α2 subunit, and the polynucleotide sequences which encode them. Also described herein are methods for producing the α2 subunit of prolyl-4-hydroxylase, prolyl-4-hydroxylase and collagen, wherein said prolyl-4-hydroxylase is comprised of the α2 subunit of the present invention and said collagen is processed into its proper form by such prolyl-4-hydroxylase. In accordance with the invention, any nucleotide sequence which encodes the amino acid sequence of claimed α2 subunit of prolyl-4-hydroxylase can be used to generate recombinant molecules which direct the expression of human prolyl-4-hydroxylase.

The present invention is further directed to the use of the coding sequence for the α2 subunit of prolyl-4hydroxylase to produce an expression vector which may be used to transform appropriate host cells. The host cells of the present invention are then induced to express the coding sequence and thereby produce the α2 subunit of prolyl-4-hydroxylase, or more generally, in combination with the β subunit, prolyl-4-hydroxylase.

4. DETAILED DESCRIPTION

The present invention relates to human α2 subunits of prolyl-4-hydroxylase and nucleic acid sequences encoding these α2 subunits of the prolyl-4-hydroxylase and derivatives thereof. In accordance with the invention, any nucleotide sequence which encodes the amino acid sequence of claimed human α2 subunit of prolyl-4-hydroxylase can be used to generate recombinant molecules which direct the expression of prolyl-4-hydroxylase. Also within the scope of the invention are methods of using and making these α2 subunit of prolyl-4hydroxylase.

a. Definitions

The term "α2 subunit of prolyl-4-hydrxylase" refers to isoforms of the α subunit of prolyl-4-hydroxylase, as encoded by a single gene as set forth at SEQ ID NO: 3, and genes which contain conservative substitutions thereto.

"Active human prolyl-4-hydroxylase" refers to a protein complex comprising a prolyl-4-hydroxylase $\alpha_2\beta_2$ tetramer, and may be recombinantly produced.

The phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5× SSC (0.75 M NaCl, 0.075 M Sodium citrate) 5× Denhardt's solution, sonicated salmon sperm DNA (50 g/ml), 0.1% SDS, and 10% dextran sulfate at 42° C., with washes at 42° C. in 0.2× SSC and 0.1% SDS.

The term "purified" as used in reference to prolyl-4-hydroxylase denotes that the indicated molecules are present in the substantial absence of other biological macromolecules, e.g., polynucleotides, proteins, and the like. The term "purified" as used herein preferably means at least 95% by weight, more preferably at least 99.8% by weight, of the indicated biological macromolecules present (but water, buffers, and other small molecules, especially molecules having a molecular weight of less than 1000 daltons can be present).

The term "isolated" as used herein refers to a protein molecule separated not only from other proteins that are present in the source of the protein, but also from other proteins, and preferably refers to a protein found in the presence of (if anything) only a solvent, buffer, ion, or other component normally present in a solution of the same. The terms "isolated" and "purified" do not encompass proteins present in their natural source.

b. BRIEF DESCRIPTION OF THE DRAWINGS

FIG. 1 (FIG. 1) sets forth the nucleotide (SEQ ID NO:1) and deduced amino acid sequence (SEQ ID NO:2) for the α(2) subunit of mouse prolyl-4-hydroxylase.

FIGS. 2A, 2B, and 2C (FIG. 2A, FIG. 2B, FIG. 2C) sets forth the nucleotide (SEQ ID NO:3) and deduced amino acid sequence (SEQ ID NO:4) for the α(2) subunit of human prolyl-4-hydroxylase, as derived from cDNA clones.

FIG. 3 (FIG. 3) sets forth the nucleotide (SEQ ID NO:5) and deduced amino acid sequence (SEQ ID NO:6) for EXON 2 (as identified in FIG. 2) and flanking intron sequences.

FIG. 4 (FIG. 4) sets forth the nucleotide ((SEQ ID NO:7) and deduced amino acid sequence (SEQ ID NO:8) for EXON 3 (as identified in FIG. 2) and flanking intron sequences.

FIG. 5 (FIG. 5) sets forth the nucleotide (SEQ ID NO:9) and deduced amino acid sequence (SEQ ID NO:10) for EXON 4 (as identified in FIG. 2) and flanking intron sequences.

FIG. 6 (FIG. 6) sets forth the nucleotide (SEQ ID NO:11) and deduced amino acid sequence (SEQ ID NO:12) for EXON 5 (as identified in FIG. 2) and flanking intron sequences.

FIG. 7 (FIG. 7) sets forth the nucleotide (SEQ ID NO:13) and deduced amino acid sequence (SEQ ID NO:14) for EXON 6 (as identified in FIG. 2) and flanking intron sequences.

FIG. 8 (FIG. 8) sets forth the nucleotide (SEQ ID NO:15) and deduced amino acid sequence (SEQ ID NO:16) for EXON 7 (as identified in FIG. 2) and flanking intron sequences.

FIGS. 9A, 9B and 9C (FIG. 9A, FIG. 9B, FIG. 9C) set forth the nucleotide (SEQ ID NO:17) and deduced amino acid sequence (SEQ ID NO:18) for EXON 8 (as identified in FIG. 2) and flanking intron sequences.

c. EXPRESSION OF THE α2 SUBUNIT OF PROLYL-4-HYDROXYLASE OF THE INVENTION (1) Coding Sequences In accordance with the invention, polynucleotide sequences which encode a human isoform of the α subunit of prolyl-4-hydroxylase, or functional equivalents thereof, may be used to generate recombinant DNA molecules that direct the expression of the human α2 subunit of prolyl-4-hydroxylase or its derivatives, and prolyl-4-hydroxylase comprising the α2 subunit of prolyl-4-hydroxylase, or a functional equivalent thereof, in appropriate host cells. Such sequences of an α2 subunit of prolyl-4-hydroxylase, as well as other polynucleotides which selectively hybridize to at least a part of such polynucleotides or their complements, may also be used in nucleic acid hybridization assays, Southern and Northern blot analyses, etc.

Due to the inherent degeneracy of the genetic code, other nucleic acid sequences which encode substantially the same or a functionally equivalent amino acid sequence, may be used in the practice of the invention for the cloning and expression of α2 subunit of prolyl-4-hydroxylase proteins. Such nucleic acid sequences include those which are capable of hybridizing to the appropriate α2 subunit of prolyl-4-hydroxylase sequence under stringent conditions.

Altered nucleic acid sequences which may be used in accordance with the invention include deletions, additions or substitutions of different nucleotide residues resulting in a sequence that encodes the same or a functionally equivalent gene product. The nucleic acid product itself may contain deletions, additions or substitutions of amino acid residues within an α2 subunit of the prolyl-4-hydroxylase sequence, which result in a silent change thus producing a functionally equivalent a subunit. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The nucleic acid sequences of the invention may be engineered in order to alter the α2 subunit of the prolyl-4-hydroxylase coding sequence for a variety of ends including but not limited to alterations which modify processing and expression of the gene product. For example, alternative secretory signals may be substituted for the native human secretory signal and/or mutations may be introduced using techniques which are well known in the art, e.g., site-directed mutagenesis, to insert new restriction sites, to alter glycosylation patterns, phosphorylation, etc.

Additionally, when expressing in non-human cells, the polynucleotides encoding the prolyl-4-hydroxylase of the invention may be modified so as to better conform to the codon preference of the particular host organism.

In an alternate embodiment of the invention, the coding sequence of the α2 subunit of prolyl-4-hydroxylase of the invention could be synthesized in whole or in part, using chemical methods well known in the art. See, for example, Caruthers et al., Nuc. Acids Res. Symp. Ser. 7:215–233 (1980); Crea and Horn, Nuc. Acids Res. 9(10):2331 (1980); Matteucci and Caruthers, Tetrahedron Letters 21:719 (1980); and Chow and Kempe, Nuc. Acids Res. 9(12):2807–2817 (1981). Alternatively, the protein itself could be produced using chemical methods to synthesize the desired α2 subunit amino acid sequence at least in part. For example, peptides can be synthesized by solid phase techniques, cleaved from the resin, and purified by preparative high performance liquid chromatography. (e.g., see Creighton, *Proteins Structures And Molecular Principles,* W. H. Freeman and Co., New York, pp. 50–60 (1983). The composition of the synthetic peptides may be confirmed by amino acid analysis or sequencing (e.g., the Edman degradation procedure; see Creighton, *Proteins, Structures and Molecular Principles,* W. H. Freeman and Co., New York, pp. 34–49 (1983).

In order to express the α2 subunit of prolyl-4-hydroxylase of the invention, the nucleotide sequence encoding the α2 subunit of prolyl-4-hydroxylase, or a functional equivalent, is inserted into an appropriate expression vector, i.e., a vector which contains the necessary elements for the transcription and translation of the inserted coding sequence.

(2) Expression Systems

Methods which are well known to those skilled in the art can be used to construct expression vectors containing an α2 subunit of prolyl-4-hydroxylase coding sequence for prolyl-4-hydroxylase and appropriate transcriptional/translational control signals. These methods include in vitro recombinant DNA techniques, synthetic techniques and in vivo recombination. See, for example, the techniques described in Maniatis et al., *Molecular Cloning A Laboratory Manual,* Cold Spring Harbor Laboratory, New York (1989) and Ausubel et al., *Current Protocols in Molecular Biology,* Greene Publishing Associates and Wiley Interscience, New York (1989).

A variety of host-expression vector systems may be utilized to express a coding sequence of an α2 subunit of prolyl-4-hydroxylase. These include but are not limited to microorganisms such as bacteria transformed with recombinant bacteriophage DNA, plasmid DNA or cosmid DNA expression vectors containing a coding sequence of an α2 subunit of prolyl-4-hydroxylase; yeast transformed with recombinant yeast expression vectors containing a coding sequence of an α2 subunit of prolyl-4-hydroxylase; insect cell systems infected with recombinant virus expression vectors (e.g., baculovirus) containing sequence encoding the α2 subunit of prolyl-4-hydroxylase; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a coding sequence of an α2 subunit of prolyl-4-hydroxylase; or animal cell systems infected with appropriate vectors, preferably semliki forest virus.

Additionally, the α2 subunit of prolyl-4-hydroxylase of the invention may be expressed in transgenic non-human animals wherein the desired enzyme product may be recovered from the milk of the transgenic animal. The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of an α2 subunit of prolyl-4-hydroxylase DNA, SV40-, BPV- and EBV-based vectors may be used with an appropriate selectable marker.

In bacterial systems a number of expression vectors may be advantageously selected depending upon the use intended for the α2 subunit of the prolyl-4-hydroxylase expressed. For example, when large quantities of the polypeptides of the invention are to be produced, vectors which direct the expression of high levels of protein products that are readily purified may be desirable. Such vectors include but are not limited to the *E. coli* expression vector pUR278 (Ruther et al., *EMBO J.* 2:1791 (1983)), in which the polypeptide coding sequence may be ligated into the vector in frame with the lac Z coding region so that a hybrid AS-lac Z protein is produced; pIN vectors (Inouye & Inouye, *Nucleic Acids Res.* 13:3101–3109 (1985); Van Heeke & Schuster, *J. Biol. Chem.* 264:5503–5509 (1989)); and the like. pGEX vectors may also be used to express foreign polypeptides as proteins with glutathione S-transferase (GST). In general, such proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

A preferred expression system is a yeast expression system. In yeast, a number of vectors containing constitutive or inducible promoters may be used. For a review see, *Current Protocols in Molecular Biology,* Vol. 2, Ed. Ausubel et al., Greene Publish. Assoc. & Wiley Interscience, Ch. 13 (1988); Grant et al., *Expression and Secretion Vectors for Yeast, in Methods in Enzymology,* Ed. Wu & Grossman, Acad. Press, New York 153:516–544 (1987); Glover, *DNA Cloning, Vol. II,* IRL Press, Washington, D.C., Ch. 3 (1986); and Bitter, Heterologous Gene Expression in Yeast, *Methods in Enzymology,* Eds. Berger & Kimmel, Acad. Press, New York 152:673–684 (1987); and *The Molecular Biology of the Yeast Saccharomyces,* Eds. Strathern et al., Cold Spring Harbor Press, Vols. I and II (1982).

A particularly preferred system useful for cloning and expression of the proteins of the invention uses host cells from the yeast Pichia. Species of non-Saccharomyces yeast such as *Pichia pastoris* appear to have special advantages in producing high yields of recombinant protein in scaled up procedures. Additionally, a Pichia expression kit is available from Invitrogen Corporation (San Diego, Calif.).

There are a number of methanol responsive genes in methylotrophic yeasts such as *Pichia pastoris,* the expression of each being controlled by methanol responsive regulatory regions (also referred to as promoters). Any of such methanol responsive promoters are suitable for use in the practice of the present invention. Examples of specific regulatory regions include the promoter for the primary alcohol oxidase gene from *Pichia pastoris* AOX1, the promoter for the secondary alcohol oxidase gene from *P. pastoris* AX02, the promoter for the dihydroxyacetone synthase gene from *P. pastoris* (DAS), the promoter for the P40 gene from *P. pastoris,* the promoter for the catalase gene from *P. pastoris,* and the like.

Typical expression in *Pichia pastoris* is obtained by the promoter from the tightly regulated AOX1 gene. See Ellis et al., *Mol. Cell. Biol.* 5:1111 (1985) and U.S. Pat. No. 4,855,231. This promoter can be induced to produce high levels of recombinant protein after addition of methanol to the culture. By subsequent manipulations of the same cells, expression of genes for the α2 subunit of prolyl-4-hydroxylase of the invention described herein is achieved under conditions where a recombinant collagen protein is adequately hydroxylated by the prolyl 4-hydroxylase of the present invention and, therefore, can fold into a stable helix that is required for the normal biological function of the collagen in forming fibrils.

Another particularly preferred yeast expression system makes use of the methylotrophic yeast *Hansenula polymorpha*. Growth on methanol results in the induction of key enzymes of the methanol metabolism, namely MOX (methanol oxidase), DAS (dihydroxyacetone synthase) and FMHD (formate dehydrogenase). These enzymes can constitute up to 30–40% of the total cell protein. The genes encoding MOX, DAS, and FMDH production are controlled by very strong promoters which are induced by growth on methanol and repressed by growth on glucose. Any or all three of these promoters may be used to obtain high level expression of heterologous nucleic acid sequences in *H. polymorpha*. The nucleic acid sequence encoding a α2 subunit of prolyl-4-hydroxylase of the invention is cloned into an expression vector under the control of an inducible *H. polymorpha* promoter. If secretion of the product is desired, a polynucleotide encoding a signal sequence for secretion in yeast, such as the *S. cerevisiae* prepro-mating factor α1, is fused in frame with the coding sequence for the α2 subunit of the prolyl-4-hydroxylase of the invention. The expression vector preferably contains an auxotrophic marker gene, such as URA3 or LEU2, which may be used to complement the deficiency of an auxotrophic host.

The expression vector is then used to transform *H. polymorpha* host cells using techniques known to those of skill in the art. An interesting and useful feature of *H. polymorpha* transformation is the spontaneous integration of up to 100 copies of the expression vector into the genome. In most cases, the integrated DNA forms multimers exhibiting a head-to-tail arrangement. The integrated foreign DNA has been shown to be mitotically stable in several recombinant strains, even under non-selective conditions. This phenomena of high copy integration further adds to the high productivity potential of the system.

In cases where plant expression vectors are used, the expression of sequences encoding the α2 subunits of the invention may be driven by any of a number of promoters. For example, viral promoters such as the 35S RNA and 19S RNA promoters of CaMV (Brisson et al., *Nature* 310:511–514 (1984), or the coat protein promoter of TMV (Takamatsu et al., *EMBO J.* 6:307–311 (1987)) may be used; alternatively, plant promoters such as the small subunit of RUBISCO (Coruzzi et al., *EMBO J.* 3:1671–1680 (1984); Broglie et al., *Science* 224:838–843 (1984); or heat shock promoters, e.g., soybean hsp17.5-E or hsp17.3-B (Gurley et al., *Mol. Cell. Biol.* 6:559–565 (1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, *Methods for Plant Molecular Biology,* Academic Press, New York, Section VIII, pp. 421–463 (1988); and Grierson & Corey, *Plant Molecular Biology,* 2d Ed., Blackie, London, Ch. 7–9 (1988).

An alternative expression system which could be used to express the α2 subunit of prolyl-4-hydroxylase of the invention is an insect system. In one such system, *Autographa californica* nuclear polyhidrosis virus (AcNPV) is used as a vector to express foreign genes. The virus grows in *Spodoptera frugiperda* cells. Coding sequence for the α2 subunit of prolyl-4-hydroxylase of the invention may be cloned into non-essential regions (for example the polyhedron gene) of the virus and placed under control of an AcNPV promoter (for example, the polyhedron promoter). Successful insertion of a α2 subunit of prolyl-4-hydroxylase coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., *J. Virol.* 46:584 (1983); Smith, U.S. Pat. No. 4,215,051).

In mammalian host cells, a number of viral based expression systems may be utilized. In cases where an adenovirus is used as an expression vector, coding sequence for the α2 subunit prolyl-4-hydroxylase of the invention may be ligated to an adenovirus transcription/translation control complex, e.g., the late promoter and tripartite leader sequence. This gene may then be inserted in the adenovirus genome by in vitro or in vivo recombination. Insertion in a non-essential region of the viral genome (e.g., region E1 or E3) will result in a recombinant virus that is viable and capable of expressing the polypeptide in infected hosts. (e.g., See Logan & Shenk, *Proc. Natl. Acad. Sci. (USA)* 81:3655–3659 (1984)). Alternatively, the vaccinia 7.5 K promoter may be used. (See, e.g., Mackett et al., *Proc. Natl. Acad. Sci. (USA)* 79:7415–7419 (1982); Mackett et al., *J. Virol.* 49:857–864 (1984); Panicali et al., *Proc. Natl. Acad. Sci.* 79:4927–4931 (1982).

Specific initiation signals may also be required for efficient translation of inserted prolyl-4-hydroxylase coding sequences. These signals include the ATG initiation codon and adjacent sequences. In cases where the entire polypeptide gene, including its own initiation codon and adjacent sequences, is inserted into the appropriate expression vector, no additional translational control signals may be needed. However, in cases where only a portion of a coding sequence is inserted, exogenous translational control signals, including the ATG initiation codon, must be provided. Furthermore, the initiation codon must be in phase with the reading frame of the α2 subunit of prolyl-4-hydroxylase coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544 (1987)).

One preferred expression system for the recombinant production of the α2 subunit of prolyl-4-hydroxylase of the invention is in transgenic non-human animals, wherein the desired polypeptide may be recovered from the milk of the transgenic animal. Such a system is constructed by operably linking the DNA sequence encoding the α2 subunit of the invention to a promoter and other required or optional regulatory sequences capable of effecting expression in mammary glands. Likewise, required or optional post-translational enzymes may be produced simultaneously in the target cells, employing suitable expression systems, as disclosed in, inter alia, U.S. application, Ser. No. 08/037,728, operable in the targeted milk protein producing mammary gland cells.

For expression in milk, the promoter of choice would preferably be from one of the abundant milk-specific proteins, such as alpha S1-casein, or β-lactoglobulin. For example, 5' and 3' regulatory sequences of alpha S1-casein have been successfully used for the expression of the human lactoferrin cDNA, and similarly, the β-lactoglobin promoter has effected the expression of human antitrypsin gene fragments in sheep milk producing cells. Wright et al., *Biotechnology* 9:830–833 (1991). In transgenic goats, the whey acid promoter has been used for the expression of human tissue plasminogen activator, resulting in the secretion of human tissue plasminogen activator in the milk of the transgenics. Ebert et al., *Biotechnology* 9:835–838 (1991). Using such expression systems, animals are obtained which secrete the polypeptides of the invention into milk. Using procedures well-known by those of the ordinary skill in the art, the gene encoding the desired prolyl-4-hydroxylase chain can simply be ligated to suitable control sequences which function in the mammary cells of the chosen animal species. Expression systems for the genes encoding the α2 subunit of prolyl-4-hydroxylase are constructed analogously.

Preferably, the prolyl-4-hydroxylase of the invention is expressed as a secreted protein. When the engineered cells used for expression of the proteins are non-human host cells, it is often advantageous to replace the human secretory signal peptide of the prolyl-4-hydroxylase protein with an alternative secretory signal peptide which is more efficiently recognized by the host cell's secretory targeting machinery. The appropriate secretory signal sequence is particularly important in obtaining optimal fungal expression of mammalian genes. For example, in methylotrophic yeasts, a DNA sequence encoding the in-reading frame *S. cerevisiae* α-mating factor pre-pro sequence may be inserted at the amino-terminal end of the coding sequence. The αMF pre-pro sequence is a leader sequence contained in the αMF precursor molecule, and includes the lys-arg encoding sequence which is necessary for proteolytic processing and secretion (see, e.g., Brake et al., *Proc. Nat'l. Acad. Sci. USA*, 81:4642 (1984)).

Also preferably, the α2 subunits of prolyl-4-hydroxylase of the present invention are co-expressed by the host cell with a β subunit of prolyl-4-hydroxylase and/or collagen, as described generally in PCT Application No. PCT/US92/09061 (WO 93/07889), such that an $\alpha_2\beta_2$ prolyl-4-hydroxylase tetramer is formed and this enzyme catalyzes the formation of 4-hydroxyproline in the expressed collagen.

Alternatively, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc. Additionally, host cells may be engineered to express various enzymes to ensure the proper processing of the collagen molecules. For example, the genes for prolyl-4-hydroxylase (i.e., the gene encoding the α subunit or prolyl-4-hydroxylase and the gene encoding the β subunit of prolyl-4-hydroxylase), may be coexpressed with the collagen gene in the host cell.

For long-term, high-yield production of recombinant proteins, stable expression is preferred. For example, cell lines which stably express an α2 subunit of prolyl-4-hydroxylase of the invention may be engineered. Rather than using expression vectors which contain viral origins of replication, host cells can be transformed with α2 subunit encoding DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a desired α2 subunit of prolyl-4-hydroxylase.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:2026 (1962)), and adenine phosphoribosyltransferase (Lowy et al., *Cell* 22:817 (1980)) genes can be employed in tk⁻, hgprt⁻ or aprt⁻ cells, respectively. Also, antimetabolite resistance can be used as the basis of selection for dhfr, which confers resistance to methotrexate (Wigler et al., *Natl. Acad. Sci. USA* 77:3567 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Colberre-Garapin et al., *J. Mol. Biol.* 150:1 (1981)); and hygro, which confers resistance to hygromycin (Santerre et al., *Gene* 30:147 (1984)). Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047 (1988)); and ODC (ornithine decarboxylase) which confers resistance to the ornithine decarboxylase inhibitor, 2-(difluoromethyl)-DL-ornithine, DFMO (McConlogue L., *In: Current Communications in Molecular Biology*, Cold Spring Harbor Laboratory, Ed.) (1987).

d. IDENTIFICATION OF TRANSFECTANTS OR TRANSFORMANTS THAT EXPRESS THE α2 SUBUNIT PROTEIN OF THE INVENTION AND PURIFICATION OF THE EXPRESSED PROTEINS

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of α2 subunit mRNA transcripts in the host cell; and (d) detection of the gene product as measured by immunoassay or by its biological activity.

In the first approach, the presence of the enzyme coding sequence inserted in the expression vector can be detected by DNA-DNA or DNA-RNA hybridization using probes comprising nucleotide sequences that are homologous to the α2 subunit of prolyl-4-hydroxylase coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the α2 subunit coding sequence is inserted within a marker gene sequence of the vector, recombinant cells containing coding sequence of the α2 subunit of prolyl-4-hydroxylase can be identified by the absence of the marker gene function. Alternatively, a marker gene can be placed in tandem with the α2 subunit sequence under the control of the same or different promoter used to control the expression of the α2 subunit coding sequence. Expression of the marker in response to induction or selection indicates expression of the α2 subunit coding sequence.

In the third approach, transcriptional activity of the α2 subunit coding region can be assessed by hybridization assays. For example, RNA can be isolated and analyzed by Northern blot using a probe homologous to the α2 subunit coding sequence or particular portions thereof. Alternatively, total nucleic acids of the host cell may be extracted and assayed for hybridization to such probes.

In the fourth approach, the expression of the enzyme product can be assessed immunologically, for example by Western blots, immunoassays such as radioimmunoprecipitation, enzyme-linked immunoassays and the like.

The expressed enzyme of the invention, which is secreted into the culture medium, is purified to homogeneity, e.g., by chromatography. In one embodiment, the recombinant α2 subunit of prolyl-4-hydroxylase protein is purified by size exclusion chromatography. However, other purification techniques known in the art can also be used, including ion exchange chromatography, and reverse-phase chromatography.

5. EXAMPLES

The invention will be further understood by reference to the following examples, which are intended to be purely exemplary of the invention.

Example 1

Isolation of Mouse cDNA Clones

A cDNA clone for the mouse α2 subunit, designated BT14.1, was obtained from a BALB/c mouse brain cDNA library in λgt10 (Clontech) by using as a probe, a cDNA encoding the thymic shared antigen 1, as described in MacNeil, et al. (1993) *J. Immunol.* 151:6913–23. The BT14.1 clone had a high degree of homology to the human and chicken prolyl-4-hydroxylase α subunit. The cDNA clone BT14.1, however, did not contain sequences coding for the N-terminal region of the polypeptide. It was therefore used as a probe to screen mouse brain and skeletal muscle cDNA libraries.

Among 600,000 recombinants, 4 positive clones were obtained. Two of them, M1 and M4 were found to be identical, while M2 had a deletion and M3 contained two unrelated inserts. The clone M1, was used to screen $1.6 \times 10^6$ plaques of a mouse skeletal muscle cDNA library in λgt10 (Clontech). One positive clone, M6, was obtained. This clone was characterized further and was found to be included in BT14.1. The 5' ends of M1 and BT14.1 were at the same internal EcoRI site (at nucleotide position 220 of the sequence shown in FIG. 1). The extreme 5' clone was isolated by using M1 to screen a mouse skeletal muscle cDNA library, and one positive clone was obtained, M6. As set forth below, at Example 2, the cDNA clones, considered in combination, cover the whole coding region of the mouse α2 subunit.

cDNA clones for the mouse α1 subunit were then isolated by screening a 3T3 fibroblast λgt11 cDNA library (Clontech) with the human cDNA clone PA-49 for the α1 subunit, as described in Helaakoski, et al. (1989) *Proc. Natl. Acad. Sci. (USA)* 86:4392–96, and eight positive clones were obtained out of 600,000 plaques.

Three of these clones, MA3, MA4, and MA7, were isolated and sequenced. The nucleotide and predicted amino acid sequences of the clones showed a significant similarity to those of the human and chick prolyl 4-hydroxylase α subunit. Two of the clones, MA3 and MA4, were found to represent the mouse counterparts of human mRNA containing the alternatively spliced exon 10 sequences, whereas MA7 contained exon 9 sequences. The cDNA clones did not contain the extreme 5' end of the mRNA. Comparison of the cDNA derived amino acid sequences with those of the human and chick α1 subunits suggests that the cDNA clones cover the whole processed polypeptide but do not cover the 5' untranslated region or the sequences corresponding to the N-terminal half of the signal peptide. See, GenBank database, accession no. U16162.

Example 2

Nucleotide Sequencing, Sequence Analysis, and Northern Blot Analysis

The nucleotide sequences for the clones described in Example 1 were determined by the dideoxynucleotide chain-termination method, as described in Sanger, et al., (1977) *Proc. Natl. Acad. Sci. (USA)* 74:5463–67, with T7 DNA polymerase (Pharmacia). Vector-specific or sequence-specific primers synthesized in an Applied Biosystems DNA synthesizer (Department of Biochemistry, University of Oulu) were used. The DNASIS and PROSIS version 6.00 sequence analysis software (Pharmacia), ANTHEPROT (as disclosed in Deleage, et al. (1988) *Comput. Appl. Biosci.* 4:351–356), the Wisconsin Genetics Computer Group package version 8 (September 1994), and BOXSHADE (Kay Hofmann, Bioinformatics Group, Institut Suisse de Recherches Experimentales sur le Cancer Lausanne, Switzerland) were used to compile the sequence data.

The cDNA clones cover 2168 not of the corresponding mRNA and encode a 537-aa polypeptide (FIG. 1). A putative signal peptide is present at the N terminus of the deduced polypeptide, the most likely first amino acid of the mature α2 subunit being tryptophan, based on the computational parameters of von Hejne (1986) *Nucleic Acid Res.* 14:4683–90, which means that the size of the signal sequence would be 19 aa and that of the processed α2 subunit 518 aa. The molecular weight of the processed polypeptide is 59,000. The cDNA clones also cover 150 bp and 407 bp of the 5' and 3' untranslated sequences, respectively (FIG. 1). The 3' untranslated sequence contains a canonical polyadenylylation signal, which is accompanied 12 nucleotides downstream by a poly(A) tail of 15 nucleotide position.

The mouse α2 and mouse α1 polypeptides are of similar sizes, α2 being 518 and α1 517 amino acids, assuming that the α2 polypeptide begins with a tryptophan residue and α1 with a histidine residue, as does the human α1 polypeptide. The processed human α1 subunit contains 517 amino acids and the chick α1 subunit 516 amino acids (as described in Bassuk, et al., supra), whereas the processed *C. elegans* α subunit is longer, 542 aa (Veijola, et al., supra), the difference being mainly due to a 32 aa extension present in the C terminus of the polypeptide (FIG. 2).

The mouse α2 and α1 subunits contain two potential attachment sites for asparagine-linked oligosaccharides; the positions of the -Asn-Leu-Ser-and -Asn-Glu-Thr- sequences of the α2 subunit are indicated in FIG. 1. The positions of the five cysteine residues present in the human, mouse, and chicken α1 subunits and the *C. elegans* α subunit are all conserved in the α2 subunit, but the latter contains an additional cysteine between the fourth and fifth cysteines of the α1 subunits. Interestingly, this is located at a site where the conserved stretch of amino acids is also interrupted in the mouse α1 and *C. elegans* α subunits.

The overall amino acid sequence identity and similarity between the mouse α2 and mouse α1 subunits are 63% and 83%, respectively, and those between the mouse α2 and *C. elegans* α subunits are 41% and 67%, respectively, which are almost the same as between the mouse α1 and *C. elegans* α subunits, 43% and 67%. The identity is not distributed equally, however, being highest within the C-terminal domain, which is believed to represent the catalytically important part of the al subunit (id.; Myllyla, et al. (1992) *Biochem. J.* 286:923–927). The two histidines, residues 412 and 483 in the mouse α1 subunit (FIG. 2), that have been suggested to be involved in the $Fe^{2+}$ binding sites of prolyl 4-hydroxylase (26) are both conserved and are both located within the conserved C-terminal domain.

A mouse multitissue Northern blot (Clontech) containing 2 µg of poly(A)' RNA per sample isolated from various mouse tissues was hybridized under the stringent conditions suggested in the manufacture's instructions. The probe used was $^{32}P$ labeled cDNA clone BT14.1 or MA7.

The expression patterns of both types of a α-subunit mRNA were found to be very similar, the intensities of the hybridization signals being highest in the heart, lung, and brain. The size of the α2 subunit mRNA was 2.4 kb. The mouse α1 subunit was found to have two mRNA transcripts, at least in the heart, brain, and lungs: the more intense the signal was at 3.4 kb and the weaker one at 4.3 kb.

Example 3

Cell Cultures and Generation of Recombinant Baculoviruses

Since it was not known initially whether the α2 polypeptide represented an α subunit of prolyl 4-hydroxylase, a subunit of prolyl 3-hydroxylase, or some other 2-oxoglutarate dioxygenase, a recombinant polypeptide was expressed in insect cells to elucidate its function. Specifically, *Spodopiera frugiperda* Sf9 insect cells were cultured at 27° C. in TNM-FH medium (Sigma) supplemented with 10% fetal bovine serum (GIBCO). To construct an α(11)-subunit cDNA for expression, the clone BT14.1 was digested with the BamHI and EcoRI restriction enzymes, giving a fragment encompassing bp 592–2168. The 5' fragment was amplified from the λ DNA of M6. The primers used were cDNA specific, M3PH (5'-AAGTTGCGGCCGCGAGCATCAGCAAGGTACTGC-3') (SEQ ID NO:19), containing an artificial Not I site and M65'PCR (5'-TGTCCGGATCCAGTTTGTACGTGTC-3') (SEQ ID NO:20), containing a natural BamHI site. PCR was performed under the conditions recommended by the supplier of the Taq polymerase (Promega), and the reactions were cycled 27 times as follows: denaturation at 94° C. for 1 min, annealing at 66° C. for 1 min, and extension at 72° C. for 3 min. The product was digested with Not I and BamHI restriction enzymes to give a fragment that extended form bp 120 to 591. The two Not I-BamHI and BamNI-EcoRI fragments were then cloned into the pBluescript vector (Stratagene), the construct was digested with Not I and EcoRV, and the resulting fragment was ligated into a Not I-Sma I site of the baculovirus transfer vector pVL1392, wherein said vector was obtained according to the methods described in Luckow and Summers, (1989) *Virology* 170:31–39. The pVI construct was cotransfected into Sf9 insect cells with a modified *Autographa californica* nuclear polyhedrosis virus DNA by using the BaclulGold transfection kit (PharMingen). The resultant viral pool was collected 4 days later, amplified, and plague purified. The recombinant virus was checked by PCR-based methods, as described in Malitschek and Schartl (1991) *BioTechniques* 11:177–178.

Example 4

Expression and Analysis of Recombinant Proteins

A recombinant baculovirus coding for the mouse α2 subunit was generated and used to infect *S. frugiperda* insect cells with or without the human PDI/β subunit, wherein the insect cells were infected at a multiplicity of 5. For production of an enzyme tetramer, the human α59 1 (see, Vuori, et al., supra) or mouse α2 viruses and the PDI/β viruses (id.) were used in a 1:1 or 2:1 ratio. The cells were harvested 72 hours after infection, homogenized in 0.01 M tris, pH 7.8/0.1 M NaCl/0.1 M glycine/10 µM dithiothreitol/0.1% Triton X-100, and centrifuged. The resulting supernatants were analyzed by SDS/8% PAGE or nondenaturing 7.5% PAGE and assayed for enzyme activities. The cell pellets were further solubilized in 1% SDS and, and the 0.1% Triton X-100-soluble and 1% SDS-soluble proteins were analyzed by SDS/PAGE under reducing for the α1 subunit of prolyl 4-hydroxylase (Veijola, et al., supra; Vuori, et al., supra; John, et al. (1993) *EMBO J.* 12:1587–95). The polypeptide formed insoluble aggregates, and efficient extraction of the recombinant mouse α2 subunit from the cell homogenates required the use of 1% SDS.

Example 5

Enzyme Activity Assays

Prolyl 4-hydroxylase activity was assayed by a method based on the decarboxylation of 2-oxoH$^{14}$C-glutarate, as disclosed in Kivirriko and Myllyla (1982) *Methods Enzymol.* 82:245–304. The $K_m$ values were determined by varying the concentration of one substrate in the presence of fixed concentrations of the second while the concentrations of the other substrates were kept constant, as set forth in Myllyla, et al., (1977) *Eur. J. Biochem.* 80:349–357.

The 0.1% Triton X-100 extracts from cell homogenates containing either the mouse-human type II or the human type I enzyme were analyzed for prolyl 4-hydroxylase activity with an assay based on the hydroxylation-coupled decarbosylation of 2-oxo[1$^{14}$C]glutarate (Kivirikko and Myllyla, supra). The activities were very similar for both.

To show that the activity of the mouse/human type 2 enzyme was prolyl 4-hydroxylase activity, the amount of 4-hydroxyproline in a (Pro-Pro-gly)$_{10}$ substrate was determined after the reaction. The values indicated that the type 2 and type 1 enzymes behaved very similarly and that the activity of the type 2 enzyme was indeed prolyl 4-hydroxylase activity. The $K_m$ values for $Fe^{2+}$, 2-oxoglutarate, and ascorbate and the $K_i$ value for pyridine-2,4,-dicarboxylate, which acts as a competitive inhibitor with respect to 2-oxoglutarate, were likewise highly similar for the two enzymes, as shown in Table I.

TABLE I $K_m$ values for cosubstrates and the peptide substrate and $K_i$ values for certain inhibitors of the human type 1 and mouse/human type 2 prolyl 4-hydroxylase tetramers.

| Cosubstrate, substrate, or inhibitor | Constant | $K_m$ or $K_i$, $\mu M$ $\alpha 1_2\beta_2$ | $\alpha 2_2\beta_2$ |
|---|---|---|---|
| $Fe^{2+}$ | $K_m$ | 4 | 4 |
| 2-Oxoglutatrate | $K_m$ | 22 | 12 |
| Ascorbate | $K_m$ | 330 | 340 |
| (Pro—Pro—Gly) | $K_m$ | 18 | 45 |
| Poly(t-proline), $M_t$ 7000 | $K_i$ | 0.5 | 300* |
| Poly(t-proline), $M_t$ 44,000 | $K_i$ | 0.02 | 30* |
| Pyridine-2,4-dicarboxylate | $K_i$ | 2 | 1 |

*Values determined as $IC_{50}$.

Notably, the values differed distinctly in that the type 2 enzyme was inhibited by poly (L-proline) only at very high concentrations. As poly (L-proline) is a well-recognized, effective competitive inhibitor of type 1 prolyl 4-hydroxylase from all vertebrate sources studied and as poly (L-proline) is an effective polypeptide substrate for all plant prolyl 4-hydroxylases studied. Such finding was unexpected. Distinct differences thus appear to exist in the structures of the peptide binding sites of various prolyl 4-hydroxylases, but no detailed data are currently available on this aspect.

Example 6

Expression of the Mouse α2 Subunit and an Active Mouse α2 PDI/β Enzyme Tetramer in Insect Cells Insect cells were coinfected with two recombinant viruses coding for the two polypeptides in order to study whether an association between the mouse α2 subunit and the human PDI/β-subunit could be achieved. A hybrid protein was formed and was soluble in a buffer containing 0.1% Triton X-100, as shown by PAGE performed under nondenaturing conditions. The mouse α2 subunit expressed alone did not give any extractable recombinant protein under the same conditions, termed here the type 1 tetramer, indicating that the hybrid protein is likely to be an $\alpha 2_2\beta_2$ tetramer, termed the type 2 tetramer. No difference was found in the association of the α2 and α1 subunits with the PDI/β subunit into the tetramer. To show that the hybrid protein formed contains the human PDI/β subunit, Western blotting was performed. When the mouse α2 subunit was expressed together with the human PDI/β subunit, the protein complex contained the PDI/β subunit.

Example 7

Isolation and Sequencing of Human α2 Subunit Gene

A human lung fibroblast genomic library (cloned in the lamda FIX vector (Stratagene)) and a human chromosome 5 library (cloned in the lamda vector Charon 40 (ATCC)) were screened with probes comprising $^{32}$P-labelled nick-translated PCR fragments corresponding to the previously characterized human prolyl-4-hydroxylase α subunit cDNA sequence.

Positive clones from both the human lung fibroblast library and the human chromosome 5 library were identified, isolated and analyzed by southern blotting. Suitable fragments were subcloned into pSP72 vector (Promega) for further analysis.

Five positive clones, designated GL-2, GL-5, GL-20, GL-141 and GL-142 were obtained from the human lung fibroblast genomic library. Two of these clones, GL-2 and GL-141 were identical. Clones corresponding to the 5' and 3'-ends of the gene encoding the α2 subunit of prolyl-4-hydroxylase were not obtained.

The human chromosome 5 library was screened twice with two separate probes. The first probe corresponded to the 5'-end of the previously characterized cDNA sequence for α2 subunit of prolyl-4-hydroxylase. The second probe corresponded to the 3'-end of the same cDNA sequence. Several positive clones were obtained, including GL-3, GL-4, GL-9, GL-11, GL-11B, and GL-156. GL-3, GL-4, GL-9 and GL-11B corresponded to the 5'-end of the protein. GL-11A and GL-156 corresponded to the 3'-end of the protein clones GL-11A and GL-156 were found to be identical.

The derived sequence corresponding to the gene is more than 30 kb in size and is comprised of 15 exons. The exons that encode solely protein sequences vary from 54 to 240 base pairs and the introns vary from 241 to at least 3200 base pairs (see, FIGS. 2–9).

As compared to the gene sequence for the α1 subunit, only one exon of the α2 subunit corresponds to the two mutually exclusive spliced exons of the α1 subunit gene (EXON 9 of the α1 subunit gene).

The deduced amino acid sequence is 63% homologous to the known α(1) subunit.

Example 8

Expression Of The Human α2 Subunit Of Prolyl-4-Hydroxylase In Insect Cells

Using the methods of Examples 3, 4 and 6, the α2 subunit isoform of prolyl-4-hydroxylase was expressed and analyzed. Expression data in insect cells demonstrated that the α2 subunit isoform forms an active type 2 prolyl-4-hydroxyl $\alpha_2\alpha_2$ tetramer with the human β subunit.

Various modifications of the invention, in addition to those shown and described herein, will become apparent to those skilled in the art from the foregoing description. Such modifications are intended to fall within the scope of the appended claims. It is also to be understood that all base pair sizes given for nucleotides are approximate and are used for purposes of description.

All references cited herein are hereby incorporated by reference in their entirety.

What is claimed is:

1. An isolated nucleic acid sequence encoding an α2 subunit of prolyl-4-hydroxylase comprising a nucleotide sequence of SEQ ID NO:3, a nucleotide sequence which is degenerate to SEQ ID NO:3, or a nucleotide sequence which is a conservative substitution variant of SEQ ID NO:3 and hybridizes to SEQ ID NO:3 under stringent conditions.

2. An expression vector comprising nucleic acid of claim 1.

3. The expression vector of claim 2 wherein said vector is further comprised of a nucleotide sequence encoding a β subunit of prolyl-4-hydroxylase.

4. A host cell infected, transformed or transfected with the expression vector of claim 2.

5. The host cell of claim 4, wherein said host cell is further infected, transformed and transfected with an expression vector comprising a nucleotide sequence encoding a β subunit of prolyl-4-hydroxylase.

6. The host cell of claim 4, wherein said host cell is further infected, transformed or transfected with an expression vector comprising one or more nucleotide sequences encoding collagen.

7. The host cell of claim 4 wherein said host cell is selected from the group consisting of insect cells, yeast, bacterial cells, plant cells, or mammalian cells.

8. A method for producing an α2 subunit of prolyl-4-hydroxylase comprising:

(a) culturing a host cell infected, transformed or transfected with an expression vector comprising a nucleic acid of claim 1; and (b) isolating said α2 subunit of prolyl-4-hydroxylase.

9. A method for producing prolyl-4-hydroxylase comprising:

(a) culturing a host cell infected, transformed or transfected with (i) an expression vector comprising a nucleic acid of claim 4; and (ii) an expression vector encoding a β subunit of prolyl-4-hydroxylase under conditions to form an $\alpha_2\beta_2$ tetramer; and (b) isolating said $\alpha_2\beta_2$ tetramer.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 2168 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 151...1761
      (D) OTHER INFORMATION:

(xi) SEQUENCE DESCRIPTION: SEQ ID NO:1:

```
GCAGTTTCAG AGACCGGTGG CGATTGGCTG ACTGATTCAA CAAATAGAGC ATTCTCTGTG      60

CCTGGAGACT TTCAAGGACT GAGGCAGGCA GAAGGGAAGA CTCAGAAAGT TCAGGTCCAG     120

AGCATCAGCA AGGTACTGCC CTTTCCAGTT  ATG AAG CTC CAG GTG TTG GTG TTG    174
                                  Met Lys Leu Gln Val Leu Val Leu
                                   1               5

GTG TTG CTG ATG TCC TGG TTC GGT GTC CTG AGC TGG GTG CAG GCA GAA     222
Val Leu Leu Met Ser Trp Phe Gly Val Leu Ser Trp Val Gln Ala Glu
     10              15                  20

TTC TTC ACC TCC ATT GGG CAC ATG ACC GAT CTG ATT TAC GCA GAG AAG     270
Phe Phe Thr Ser Ile Gly His Met Thr Asp Leu Ile Tyr Ala Glu Lys
 25              30                  35                  40

GAC CTG GTA CAG TCT CTG AAG GAG TAC ATC CTT GTG GAG GAA GCC AAG     318
Asp Leu Val Gln Ser Leu Lys Glu Tyr Ile Leu Val Glu Glu Ala Lys
                 45                  50                  55

CTC GCC AAG ATT AAG AGC TGG GCC AGC AAG ATG GAA GCC CTG ACC AGC     366
Leu Ala Lys Ile Lys Ser Trp Ala Ser Lys Met Glu Ala Leu Thr Ser
             60                  65                  70

AGA TCA GCT GCC GAC CCC GAG GGC TAC CTG GCT CAT CCT GTG AAT GCC     414
Arg Ser Ala Ala Asp Pro Glu Gly Tyr Leu Ala His Pro Val Asn Ala
         75                  80                  85

TAC AAG CTG GTG AAG CGG TTG AAC ACA GAC TGG CCT GCA CTG GGG GAC     462
Tyr Lys Leu Val Lys Arg Leu Asn Thr Asp Trp Pro Ala Leu Gly Asp
 90                  95                 100

CTT GTC CTT CAG GAT GCT TCG GCA GGT TTT GTC GCT AAC CTC TCA GTT     510
Leu Val Leu Gln Asp Ala Ser Ala Gly Phe Val Ala Asn Leu Ser Val
105                 110                 115                 120

CAG CGG CAA TTC TTC CCC ACT GAT GAG GAC GAG TCT GGA GCT GCC AGA     558
Gln Arg Gln Phe Phe Pro Thr Asp Glu Asp Glu Ser Gly Ala Ala Arg
                125                 130                 135

GCC CTG ATG AGA CTT CAG GAC ACG TAC AAA CTG GAT CCG GAC ACG ATT     606
Ala Leu Met Arg Leu Gln Asp Thr Tyr Lys Leu Asp Pro Asp Thr Ile
            140                 145                 150

TCC AGA GGG GAA CTT CCA GGC ACA AAG TAC CAG GCC ATG CTG AGT GTG     654
Ser Arg Gly Glu Leu Pro Gly Thr Lys Tyr Gln Ala Met Leu Ser Val
        155                 160                 165

GAC GAC TGC TTT GGG CTG GGC CGC TCA GCT TAC AAT GAA GGA GAC TAT     702
Asp Asp Cys Phe Gly Leu Gly Arg Ser Ala Tyr Asn Glu Gly Asp Tyr
    170                 175                 180

TAC CAT ACT GTG CTG TGG ATG GAG CAG GTA CTG AAG CAG CTC GAT GCT     750
Tyr His Thr Val Leu Trp Met Glu Gln Val Leu Lys Gln Leu Asp Ala
185                 190                 195                 200

GGG GAG GAG GCC ACT GTT ACC AAG TCC CTG GTG CTG GAC TAC CTG AGC     798
```

-continued

```
Gly Glu Glu Ala Thr Val Thr Lys Ser Leu Val Leu Asp Tyr Leu Ser
            205             210             215

TAT GCT GTC TTC CAA CTG GGT GAC CTG CAC CGT GCT GTG GAA CTC ACC        846
Tyr Ala Val Phe Gln Leu Gly Asp Leu His Arg Ala Val Glu Leu Thr
            220             225             230

CGC CGC CTG CTC TCT CTT GAC CCA AGC CAC GAA CGA GCT GGA GGG AAT        894
Arg Arg Leu Leu Ser Leu Asp Pro Ser His Glu Arg Ala Gly Gly Asn
            235             240             245

CTG CGG TAC TTT GAA CGG TTG TTA GAG GAA GAA AGA GGG AAA TCA CTG        942
Leu Arg Tyr Phe Glu Arg Leu Leu Glu Glu Glu Arg Gly Lys Ser Leu
            250             255             260

TCA AAT CAG ACA GAC GCC GGA CTG GCC ACC CAG GAA AAC TTG TAC GAG        990
Ser Asn Gln Thr Asp Ala Gly Leu Ala Thr Gln Glu Asn Leu Tyr Glu
265             270             275             280

AGG CCC ACG GAC TAC CTG CCT GAG AGG GAT GTG TAC GAG AGC CTG TGT       1038
Arg Pro Thr Asp Tyr Leu Pro Glu Arg Asp Val Tyr Glu Ser Leu Cys
            285             290             295

CGA GGG GAG GGC GTG AAA CTG ACA CCC CGG AGG CAG AAG AAG CTT TTC       1086
Arg Gly Glu Gly Val Lys Leu Thr Pro Arg Arg Gln Lys Lys Leu Phe
            300             305             310

TGT AGG TAC CAT CAT GGA AAC AGA GTG CCA CAG CTC CTC ATC GCC CCC       1134
Cys Arg Tyr His His Gly Asn Arg Val Pro Gln Leu Leu Ile Ala Pro
            315             320             325

TTC AAA GAG GAA GAC GAG TGG GAC AGC CCA CAC ATC GTC AGG TAC TAT       1182
Phe Lys Glu Glu Asp Glu Trp Asp Ser Pro His Ile Val Arg Tyr Tyr
            330             335             340

GAT GTG ATG TCC GAC GAA GAA ATC GAG AGG ATC AAG GAG ATT GCT AAG       1230
Asp Val Met Ser Asp Glu Glu Ile Glu Arg Ile Lys Glu Ile Ala Lys
345             350             355             360

CCC AAA CTT GCA CGA GCC ACT GTG CGT GAC CCC AAG ACA GGT GTC CTC       1278
Pro Lys Leu Ala Arg Ala Thr Val Arg Asp Pro Lys Thr Gly Val Leu
            365             370             375

ACT GTT GCC AGC TAC AGA GTT TCC AAA AGC TCC TGG CTA GAG GAG GAT       1326
Thr Val Ala Ser Tyr Arg Val Ser Lys Ser Ser Trp Leu Glu Glu Asp
            380             385             390

GAC GAC CCT GTT GTG GCC CGG GTC AAC CGG CGG ATG CAA CAT ATC ACC       1374
Asp Asp Pro Val Val Ala Arg Val Asn Arg Arg Met Gln His Ile Thr
            395             400             405

GGG CTA ACG GTG AAG ACT GCA GAG CTA TTG CAG GTC GCA AAC TAC GGA       1422
Gly Leu Thr Val Lys Thr Ala Glu Leu Leu Gln Val Ala Asn Tyr Gly
            410             415             420

ATG GGG GGA CAG TAC GAA CCA CAC TTT GAC TTC TCA AGG AGC GAT GAC       1470
Met Gly Gly Gln Tyr Glu Pro His Phe Asp Phe Ser Arg Ser Asp Asp
425             430             435             440

GAA GAT GCT TTC AAG CGT TTA GGG ACT GGG AAC CGT GTG GCC ACG TTT       1518
Glu Asp Ala Phe Lys Arg Leu Gly Thr Gly Asn Arg Val Ala Thr Phe
            445             450             455

CTA AAC TAC ATG AGC GAT GTC GAA GCT GGT GGT GCC ACC GTC TTT CCT       1566
Leu Asn Tyr Met Ser Asp Val Glu Ala Gly Gly Ala Thr Val Phe Pro
            460             465             470

GAC TTG GGA GCT GCT ATT TGG CCC AAG AAG GGC ACA GCT GTA TTC TGG       1614
Asp Leu Gly Ala Ala Ile Trp Pro Lys Lys Gly Thr Ala Val Phe Trp
            475             480             485

TAC AAC CTT CTT CGC AGT GGG GAA GGT GAT TAT CGG ACG AGA CAT GCA       1662
Tyr Asn Leu Leu Arg Ser Gly Glu Gly Asp Tyr Arg Thr Arg His Ala
            490             495             500

GCC TGC CCT GTG CTT GTG GGC TGC AAG TGG GTC TCC AAC AAG TGG TTC       1710
Ala Cys Pro Val Leu Val Gly Cys Lys Trp Val Ser Asn Lys Trp Phe
505             510             515             520

CAT GAG CGA GGA CAG GAG TTC TTA AGA CCT TGT GGA ACA ACG GAA GTT       1758
```

```
His Glu Arg Gly Gln Glu Phe Leu Arg Pro Cys Gly Thr Thr Glu Val
                525                 530                 535

GAT  TGACGTCCTT  TTCTCTCCGC  TCCTCCCTGG  CCCATAGTCC  AAATCATCTT  CAAGTT    1817
Asp

CAACATGACA  GCTTCCTTTT  TTATGTCCCA  GCTCCTGTCA  GGCAGGTCAT  TGGAGGAGCC    1877

AGTGTTTGAC  TGAATTGAGA  GAGTATATCC  TGAGCCTAGT  CCTGGGTGAC  CTGGGCCCCA    1937

GACTCTGACC  AGCTTACACC  TGCCCTGGCT  CTGGGGGTGT  CTTGGCATGG  CTGCGGTAGA    1997

GCCAGACTAT  AGCACCCGGC  ACGGTCGCTT  TGTACCTCAG  ATATTTCAGG  TAGAAGATGT    2057

CTCAGTGAAA  CCAAAGTTCT  GATGCTGTTT  ACATGTGTGT  TTTTATCACA  TTTCTATTTG    2117

TTGTGGCTTT  AACCAAAAAA  TAAAAATGTT  CCTGCCAAAA  AAAAAAAAA  A              2168

(2) INFORMATION FOR SEQ ID NO:2:

(i) SEQUENCE CHARACTERISTICS:
        (A) LENGTH: 537 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Lys Leu Gln Val Leu Val Leu Leu Met Ser Trp Phe Gly
 1               5                  10                  15

Val Leu Ser Trp Val Gln Ala Glu Phe Phe Thr Ser Ile Gly His Met
                20                  25                  30

Thr Asp Leu Ile Tyr Ala Glu Lys Asp Leu Val Gln Ser Leu Lys Glu
            35                  40                  45

Tyr Ile Leu Val Glu Glu Ala Lys Leu Ala Lys Ile Lys Ser Trp Ala
50                  55                  60

Ser Lys Met Glu Ala Leu Thr Ser Arg Ser Ala Ala Asp Pro Glu Gly
65                  70                  75                  80

Tyr Leu Ala His Pro Val Asn Ala Tyr Lys Leu Val Lys Arg Leu Asn
                85                  90                  95

Thr Asp Trp Pro Ala Leu Gly Asp Leu Val Leu Gln Asp Ala Ser Ala
            100                 105                 110

Gly Phe Val Ala Asn Leu Ser Val Gln Arg Gln Phe Phe Pro Thr Asp
        115                 120                 125

Glu Asp Glu Ser Gly Ala Ala Arg Ala Leu Met Arg Leu Gln Asp Thr
130                 135                 140

Tyr Lys Leu Asp Pro Asp Thr Ile Ser Arg Gly Glu Leu Pro Gly Thr
145                 150                 155                 160

Lys Tyr Gln Ala Met Leu Ser Val Asp Asp Cys Phe Gly Leu Gly Arg
                165                 170                 175

Ser Ala Tyr Asn Glu Gly Asp Tyr Tyr His Thr Val Leu Trp Met Glu
            180                 185                 190

Gln Val Leu Lys Gln Leu Asp Ala Gly Glu Glu Ala Thr Val Thr Lys
        195                 200                 205

Ser Leu Val Leu Asp Tyr Leu Ser Tyr Ala Val Phe Gln Leu Gly Asp
    210                 215                 220

Leu His Arg Ala Val Glu Leu Thr Arg Arg Leu Leu Ser Leu Asp Pro
225                 230                 235                 240

Ser His Glu Arg Ala Gly Gly Asn Leu Arg Tyr Phe Glu Arg Leu Leu
                245                 250                 255
```

```
Glu Glu Glu Arg Gly Lys Ser Leu Ser Asn Gln Thr Asp Ala Gly Leu
            260                 265                 270

Ala Thr Gln Glu Asn Leu Tyr Glu Arg Pro Thr Asp Tyr Leu Pro Glu
            275                 280                 285

Arg Asp Val Tyr Glu Ser Leu Cys Arg Gly Glu Gly Val Lys Leu Thr
            290                 295             300

Pro Arg Arg Gln Lys Lys Leu Phe Cys Arg Tyr His His Gly Asn Arg
305                 310                 315                 320

Val Pro Gln Leu Leu Ile Ala Pro Phe Lys Glu Asp Glu Trp Asp
                325                 330                 335

Ser Pro His Ile Val Arg Tyr Tyr Asp Val Met Ser Asp Glu Ile
            340                 345             350

Glu Arg Ile Lys Glu Ile Ala Lys Pro Lys Leu Ala Arg Ala Thr Val
            355                 360             365

Arg Asp Pro Lys Thr Gly Val Leu Thr Val Ala Ser Tyr Arg Val Ser
            370                 375             380

Lys Ser Ser Trp Leu Glu Glu Asp Asp Pro Val Val Ala Arg Val
385                 390                 395                 400

Asn Arg Arg Met Gln His Ile Thr Gly Leu Thr Val Lys Thr Ala Glu
                405                 410             415

Leu Leu Gln Val Ala Asn Tyr Gly Met Gly Gln Tyr Glu Pro His
                420             425             430

Phe Asp Phe Ser Arg Ser Asp Asp Glu Asp Ala Phe Lys Arg Leu Gly
            435                 440             445

Thr Gly Asn Arg Val Ala Thr Phe Leu Asn Tyr Met Ser Asp Val Glu
450                 455                 460

Ala Gly Gly Ala Thr Val Phe Pro Asp Leu Gly Ala Ala Ile Trp Pro
465                 470                 475                 480

Lys Lys Gly Thr Ala Val Phe Trp Tyr Asn Leu Leu Arg Ser Gly Glu
                485                 490             495

Gly Asp Tyr Arg Thr Arg His Ala Ala Cys Pro Val Leu Val Gly Cys
            500                 505             510

Lys Trp Val Ser Asn Lys Trp Phe His Glu Arg Gly Gln Glu Phe Leu
            515                 520             525

Arg Pro Cys Gly Thr Thr Glu Val Asp
530                 535

(2) INFORMATION FOR SEQ ID NO:3:

(i) SEQUENCE CHARACTERISTICS:
        (A) LENGTH: 2194 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 188...1792
        (D) OTHER INFORMATION:

(xi) SEQUENCE DESCRIPTION: SEQ ID NO:3:

GGGGAAGGAA CACTGTAGGG GATAGCTGTC CACGGACGCT GTCTACAAGA CCCTGGAGTG      60

AGATAACGTG CCTGGTACTG TGCCCTGCAT GTGTAAGATG CCCAGTTGAC CTTCGCAGCA    120

GGAGCCTGGA TCAGGCACTT CCTGCCTCAG GTATTGCTGG ACAGCCCAGA CACTTCCCTC    180

TGTGACC ATG AAA CTC TGG GTG TCT GCA TTG CTG ATG GCC TGG TTT GGT      229
        Met Lys Leu Trp Val Ser Ala Leu Leu Met Ala Trp Phe Gly
          1               5                  10
```

-continued

| | |
|---|---|
| GTC CTG AGC TGT GTG CAG GCC GAA TTC TTC ACC TCT ATT GGG CAC ATG<br>Val Leu Ser Cys Val Gln Ala Glu Phe Phe Thr Ser Ile Gly His Met<br>15                 20                 25                 30 | 277 |
| ACT GAC CTG ATT TAT GCA GAG AAA GAG CTG GTG CAG TCT CTG AAA GAG<br>Thr Asp Leu Ile Tyr Ala Glu Lys Glu Leu Val Gln Ser Leu Lys Glu<br>                35                 40                 45 | 325 |
| TAC ATC CTT GTG GAG GAA GCC AAG CTT TCC AAG ATT AAG AGC TGG GCC<br>Tyr Ile Leu Val Glu Glu Ala Lys Leu Ser Lys Ile Lys Ser Trp Ala<br>        50                 55                 60 | 373 |
| AAC AAA ATG GAA GCC TTG ACT AGC AAG TCA GCT GCT GAT GCT GAG GGC<br>Asn Lys Met Glu Ala Leu Thr Ser Lys Ser Ala Ala Asp Ala Glu Gly<br>                65                 70                 75 | 421 |
| TAC CTG GCT CAC CCT GTG AAT GCC TAC AAA CTG GTG AAG CGG CTA AAC<br>Tyr Leu Ala His Pro Val Asn Ala Tyr Lys Leu Val Lys Arg Leu Asn<br>        80                 85                 90 | 469 |
| ACA GAC TGG CCT GCG CTG GAG GAC CTT GTC CTG CAG GAC TCA GCT GCA<br>Thr Asp Trp Pro Ala Leu Glu Asp Leu Val Leu Gln Asp Ser Ala Ala<br>95                 100               105             110 | 517 |
| GGT TTT ATC GCC AAC CTC TCT GTG CAG CGG CAG TTC TTC CCC ACT GAT<br>Gly Phe Ile Ala Asn Leu Ser Val Gln Arg Gln Phe Phe Pro Thr Asp<br>                115               120             125 | 565 |
| GAG GAC GAG ATA GGA GCT GCC AAA GCC CTG ATG AGA CTT CAG GAC ACA<br>Glu Asp Glu Ile Gly Ala Ala Lys Ala Leu Met Arg Leu Gln Asp Thr<br>            130               135               140 | 613 |
| TAC AGG CTG GAC CCA GGC ACA ATT TCC AGA GGG GAA CTT CCA GGA ACC<br>Tyr Arg Leu Asp Pro Gly Thr Ile Ser Arg Gly Glu Leu Pro Gly Thr<br>                145               150             155 | 661 |
| AAG TAC CAG GCA ATG CTG AGT GTG GAT GAC TGC TTT GGG ATG GGC CGC<br>Lys Tyr Gln Ala Met Leu Ser Val Asp Asp Cys Phe Gly Met Gly Arg<br>        160                 165               170 | 709 |
| TCG GCC TAC AAT GAA GGG GAC TAT TAT CAT ACG GTG TTG TGG ATG GAG<br>Ser Ala Tyr Asn Glu Gly Asp Tyr Tyr His Thr Val Leu Trp Met Glu<br>175                 180               185             190 | 757 |
| CAG GTG CTA AAG CAG CTT GAT GCC GGG GAG GAG GCC ACC ACA ACC AAG<br>Gln Val Leu Lys Gln Leu Asp Ala Gly Glu Glu Ala Thr Thr Thr Lys<br>                195               200             205 | 805 |
| TCA CAG GTG CTG GAC TAC CTC AGC TAT GCT GTC TTC CAG TTG GGT GAT<br>Ser Gln Val Leu Asp Tyr Leu Ser Tyr Ala Val Phe Gln Leu Gly Asp<br>            210               215               220 | 853 |
| CTG CAC CGT GCC CTG GAG CTC ACC CGC CGC CTG CTC TCC CTT GAC CCA<br>Leu His Arg Ala Leu Glu Leu Thr Arg Arg Leu Leu Ser Leu Asp Pro<br>        225                 230               235 | 901 |
| AGC CAC GAA CGA GCT GGA GGG AAT CTG CGG TAC TTT GAG CAG TTA TTG<br>Ser His Glu Arg Ala Gly Gly Asn Leu Arg Tyr Phe Glu Gln Leu Leu<br>        240                 245               250 | 949 |
| GAG GAA GAG AGA GAA AAA ACG TTA ACA AAT CAG ACA GAA GCT GAG CTA<br>Glu Glu Glu Arg Glu Lys Thr Leu Thr Asn Gln Thr Glu Ala Glu Leu<br>255                 260               265             270 | 997 |
| GCA ACC CCA GAA GGC ATC TAT GAG AGG CCT GTG GAC TAC CTG CCT GAG<br>Ala Thr Pro Glu Gly Ile Tyr Glu Arg Pro Val Asp Tyr Leu Pro Glu<br>                275               280             285 | 1045 |
| AGG GAT GTT TAC GAG AGC CTC TGT CGT GGG GAG GGT GTC AAA CTG ACA<br>Arg Asp Val Tyr Glu Ser Leu Cys Arg Gly Glu Gly Val Lys Leu Thr<br>        290                 295               300 | 1093 |
| CCC CGT AGA CAG AAG AGG CTT TTC TGT AGG TAC CAC CAT GGC AAC AGG<br>Pro Arg Arg Gln Lys Arg Leu Phe Cys Arg Tyr His His Gly Asn Arg<br>                305               310             315 | 1141 |
| GCC CCA CAG CTG CTC ATT GCC CCC TTC AAA GAG GAG GAC GAG TGG GAC<br>Ala Pro Gln Leu Leu Ile Ala Pro Phe Lys Glu Glu Asp Glu Trp Asp<br>        320                 325               330 | 1189 |

```
AGC CCG CAC ATC GTC AGG TAC TAC GAT GTC ATG TCT GAT GAG GAA ATC        1237
Ser Pro His Ile Val Arg Tyr Tyr Asp Val Met Ser Asp Glu Glu Ile
335                 340                 345                 350

GAG AGG ATC AAG GAG ATC GCA AAA CCT AAA CTT GCA CGA GCC ACC GTT        1285
Glu Arg Ile Lys Glu Ile Ala Lys Pro Lys Leu Ala Arg Ala Thr Val
                355                 360                 365

CGT GAT CCC AAG ACA GGA GTC CTC ACT GTC GCC AGC TAC CGG GTT TCC        1333
Arg Asp Pro Lys Thr Gly Val Leu Thr Val Ala Ser Tyr Arg Val Ser
            370                 375                 380

AAA AGC TCC TGG CTA GAG GAA GAT GAT GAC CCT GTT GTG GCC CGA GTA        1381
Lys Ser Ser Trp Leu Glu Glu Asp Asp Asp Pro Val Val Ala Arg Val
        385                 390                 395

AAT CGT CGG ATG CAG CAT ATC ACA GGG TTA ACA GTA AAG ACT GCA GAA        1429
Asn Arg Arg Met Gln His Ile Thr Gly Leu Thr Val Lys Thr Ala Glu
    400                 405                 410

TTG TTA CAG GTT GCA AAT TAT GGA GTG GGA GGA CAG TAT GAA CCG CAC        1477
Leu Leu Gln Val Ala Asn Tyr Gly Val Gly Gly Gln Tyr Glu Pro His
415                 420                 425                 430

TTC GAC TTC TCT AGG AAT GAT GAG CGA GAT ACT TTC AAG CAT TTA GGG        1525
Phe Asp Phe Ser Arg Asn Asp Glu Arg Asp Thr Phe Lys His Leu Gly
                435                 440                 445

ACG GGG AAT CGT GTG GCT ACT TTC TTA AAC TAC ATG AGT GAT GTA GAA        1573
Thr Gly Asn Arg Val Ala Thr Phe Leu Asn Tyr Met Ser Asp Val Glu
            450                 455                 460

GCT GGT GGT GCC ACC GTC TTC CCT GAT CTG GGG GCT GCA ATT TGG CCT        1621
Ala Gly Gly Ala Thr Val Phe Pro Asp Leu Gly Ala Ala Ile Trp Pro
        465                 470                 475

AAG AAG GGT ACA GCT GTG TTC TGG TAC AAC CTC TTG CGG AGC GGG GAA        1669
Lys Lys Gly Thr Ala Val Phe Trp Tyr Asn Leu Leu Arg Ser Gly Glu
    480                 485                 490

GGT GAC TAC CGA ACA AGA CAT GCT GCC TGC CCT GTG CTT GTG GGC TGC        1717
Gly Asp Tyr Arg Thr Arg His Ala Ala Cys Pro Val Leu Val Gly Cys
495                 500                 505                 510

AAG TGG GTC TCC AAT AAG TGG TTC CAT GAA CGA GGA CAG GAG TTC TTG        1765
Lys Trp Val Ser Asn Lys Trp Phe His Glu Arg Gly Gln Glu Phe Leu
                515                 520                 525

AGA CCT TGT GGA TCA ACA GAA GTT GAC TGACATCCTT TTCTGTCCTT CCCCTTC      1819
Arg Pro Cys Gly Ser Thr Glu Val Asp
            530                 535

CTGGTCCTTC AGCCCATGTC AACGTGACAG ACACCTTTGT ATGTTCCTTG TATGTTCCTA      1879

TCAGGCTGAT TTTTGGAGAA ATGAATGTTT GTCTGGAGCA GAGGGAGACC ATACTAGGGC      1939

GACTCCTGTG TGACTGAAGT CCCAGCCCTT CCATTCAGCC TGTGCCATCC CTGGCCCCAA      1999

GGCTAGGATC AAAGTGGCTG CAGCAGAGTT AGCTGTCTAG CGCCTAGCAA GGTGCCTTTG      2059

TACCTCAGGT GTTTTAGGTG TGAGATGTTT CAGTGAACCA AAGTTCTGAT ACCTTGTTTA      2119

CATGTTTGTT TTTATGGCAT TTCTATCTAT TGTGGCTTTA CCAAAAAATA AAATGTCCCT      2179

ACCAGAAGCC TTAAA                                                       2194

(2) INFORMATION FOR SEQ ID NO:4:

(i) SEQUENCE CHARACTERISTICS:
        (A) LENGTH: 535 amino acids
        (B) TYPE: amino acid
        (C) STRANDEDNESS: single
        (D) TOPOLOGY: linear (ii) MOLECULE TYPE: protein (v) FRAGMENT TYPE: internal
```

(xi) SEQUENCE DESCRIPTION: SEQ ID NO:4:

```
Met Lys Leu Trp Val Ser Ala Leu Leu Met Ala Trp Phe Gly Val Leu
 1               5                  10                  15

Ser Cys Val Gln Ala Glu Phe Phe Thr Ser Ile Gly His Met Thr Asp
                20                  25                  30

Leu Ile Tyr Ala Glu Lys Glu Leu Val Gln Ser Leu Lys Glu Tyr Ile
            35                  40                  45

Leu Val Glu Glu Ala Lys Leu Ser Lys Ile Lys Ser Trp Ala Asn Lys
 50                  55                  60

Met Glu Ala Leu Thr Ser Lys Ser Ala Ala Asp Ala Glu Gly Tyr Leu
 65                  70                  75                  80

Ala His Pro Val Asn Ala Tyr Lys Leu Val Lys Arg Leu Asn Thr Asp
                85                  90                  95

Trp Pro Ala Leu Glu Asp Leu Val Leu Gln Asp Ser Ala Ala Gly Phe
                100                 105                 110

Ile Ala Asn Leu Ser Val Gln Arg Gln Phe Phe Pro Thr Asp Glu Asp
            115                 120                 125

Glu Ile Gly Ala Ala Lys Ala Leu Met Arg Leu Gln Asp Thr Tyr Arg
130                 135                 140

Leu Asp Pro Gly Thr Ile Ser Arg Gly Glu Leu Pro Gly Thr Lys Tyr
145                 150                 155                 160

Gln Ala Met Leu Ser Val Asp Asp Cys Phe Gly Met Gly Arg Ser Ala
                165                 170                 175

Tyr Asn Glu Gly Asp Tyr Tyr His Thr Val Leu Trp Met Glu Gln Val
            180                 185                 190

Leu Lys Gln Leu Asp Ala Gly Glu Ala Thr Thr Thr Lys Ser Gln
            195                 200                 205

Val Leu Asp Tyr Leu Ser Tyr Ala Val Phe Gln Leu Gly Asp Leu His
210                 215                 220

Arg Ala Leu Glu Leu Thr Arg Arg Leu Leu Ser Leu Asp Pro Ser His
225                 230                 235                 240

Glu Arg Ala Gly Gly Asn Leu Arg Tyr Phe Glu Gln Leu Leu Glu Glu
                245                 250                 255

Glu Arg Glu Lys Thr Leu Thr Asn Gln Thr Glu Ala Glu Leu Ala Thr
                260                 265                 270

Pro Glu Gly Ile Tyr Glu Arg Pro Val Asp Tyr Leu Pro Glu Arg Asp
                275                 280                 285

Val Tyr Glu Ser Leu Cys Arg Gly Glu Gly Val Lys Leu Thr Pro Arg
290                 295                 300

Arg Gln Lys Arg Leu Phe Cys Arg Tyr His His Gly Asn Arg Ala Pro
305                 310                 315                 320

Gln Leu Leu Ile Ala Pro Phe Lys Glu Glu Asp Glu Trp Asp Ser Pro
                325                 330                 335

His Ile Val Arg Tyr Asp Val Met Ser Asp Glu Glu Ile Glu Arg
                340                 345                 350

Ile Lys Glu Ile Ala Lys Pro Lys Leu Ala Arg Ala Thr Val Arg Asp
            355                 360                 365

Pro Lys Thr Gly Val Leu Thr Val Ala Ser Tyr Arg Val Ser Lys Ser
370                 375                 380

Ser Trp Leu Glu Glu Asp Asp Pro Val Val Ala Arg Val Asn Arg
385                 390                 395                 400

Arg Met Gln His Ile Thr Gly Leu Thr Val Lys Thr Ala Glu Leu Leu
                405                 410                 415
```

```
Gln Val Ala Asn Tyr Gly Val Gly Gln Tyr Glu Pro His Phe Asp
        420                 425                 430

Phe Ser Arg Asn Asp Glu Arg Asp Thr Phe Lys His Leu Gly Thr Gly
        435                 440                 445

Asn Arg Val Ala Thr Phe Leu Asn Tyr Met Ser Asp Val Glu Ala Gly
450                 455                 460

Gly Ala Thr Val Phe Pro Asp Leu Gly Ala Ala Ile Trp Pro Lys Lys
465                 470                 475                 480

Gly Thr Ala Val Phe Trp Tyr Asn Leu Leu Arg Ser Gly Glu Gly Asp
        485                 490                 495

Tyr Arg Thr Arg His Ala Ala Cys Pro Val Leu Val Gly Cys Lys Trp
        500                 505                 510

Val Ser Asn Lys Trp Phe His Glu Arg Gly Gln Glu Phe Leu Arg Pro
        515                 520                 525

Cys Gly Ser Thr Glu Val Asp
        530                 535
```

(2) INFORMATION FOR SEQ ID NO:5:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 188...271
        (D) OTHER INFORMATION:

(xi) SEQUENCE DESCRIPTION: SEQ ID NO:5:

```
GGGGAAGGAA CACTGTAGGG GATAGCTGTC CACGGACGCT GTCTACAAGA CCCTGGAGTG      60

AGATAACGTG CCTGGTACTG TGCCCTGCAT GTGTAAGATG CCCAGTTGAC CTTCGCAGCA     120

GGAGCCTGGA TCAGGCACTT CCTGCCTCAG GTATTGCTGG ACAGCCCAGA CACTTCCCTC     180

TGTGACC ATG AAA CTC TGG GTG TCT GCA TTG CTG ATG GCC TGG TTT GGT       229
        Met Lys Leu Trp Val Ser Ala Leu Leu Met Ala Trp Phe Gly
        1                5                  10

GTC CTG AGC TGT GTG CAG GCC GAA TTC TTC ACC TCT ATT GGT ACGTGCCAA     280
Val Leu Ser Cys Val Gln Ala Glu Phe Phe Thr Ser Ile Gly
15              20                  25

CAGGACTGTC GTCTCCCTGA CACCTTGGCT CACATGCCAC GGATGTCTCT GGCTGCAGCT     340

GTTCTCATTT AGAGTGGGAT AGCCTTAACA TACGG                                375
```

(2) INFORMATION FOR SEQ ID NO:6:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

```
Met Lys Leu Trp Val Ser Ala Leu Leu Met Ala Trp Phe Gly Val Leu
1               5                   10                  15

Ser Cys Val Gln Ala Glu Phe Phe Thr Ser Ile Gly
            20                  25
```

(2) INFORMATION FOR SEQ ID NO:7:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 3...95
        (D) OTHER INFORMATION:

(xi) SEQUENCE DESCRIPTION: SEQ ID NO:7:

```
GG CAC ATG ACT GAC CTG ATT TAT GCA GAG AAA GAG CTG GTG CAG TCT         47
   His Met Thr Asp Leu Ile Tyr Ala Glu Lys Glu Leu Val Gln Ser
    1               5                  10                  15

CTG AAA GAG TAC ATC CTT GTG GAG GAA GCC AAG CTT TCC AAG ATT AAG A      96
Leu Lys Glu Tyr Ile Leu Val Glu Glu Ala Lys Leu Ser Lys Ile Lys
                20                  25                  30

GGTGTCCTAA GTCCCCATAC CATCCTTAGT TGGCCTTCCT TCCCTTCTGC CCTCAAGGAA    156

CAAGGAAGCC ATCAGGGTGC CTATAACATT AAACCTTTGA GAGG                     200
```

(2) INFORMATION FOR SEQ ID NO:8:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:8:

```
His Met Thr Asp Leu Ile Tyr Ala Glu Lys Glu Leu Val Gln Ser Leu
 1               5                  10                  15

Lys Glu Tyr Ile Leu Val Glu Glu Ala Lys Leu Ser Lys Ile Lys
                20                  25                  30
```

(2) INFORMATION FOR SEQ ID NO:9:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 81...233
        (D) OTHER INFORMATION:

(xi) SEQUENCE DESCRIPTION: SEQ ID NO:9:

```
GGGAATTCTC ACTAGAAAAT TGTCACAGGT CAAGACCTAT GTGGGTGGAC GCATTAGTCT      60

TCCTTTTCCT CTGGTTCCAC AGC TGG GCC AAC AAA ATG GAA GCC TTG ACT        110
                       Ser Trp Ala Asn Lys Met Glu Ala Leu Thr
                        1               5                  10

AGC AAG TCA GCT GCT GAT GCT GAG GGC TAC CTG GCT CAC CCT GTG AAT      158
Ser Lys Ser Ala Ala Asp Ala Glu Gly Tyr Leu Ala His Pro Val Asn
                15                  20                  25

GCC TAC AAA CTG GTG AAG CGG CTA AAC ACA GAC TGG CCT GCG CTG GAG      206
Ala Tyr Lys Leu Val Lys Arg Leu Asn Thr Asp Trp Pro Ala Leu Glu
            30                  35                  40

GAC CTT GTC CTG CAG GAC TCA GCT GCA GGTGAGGGAC GGTGACGAGG TGCTTGA    260
Asp Leu Val Leu Gln Asp Ser Ala Ala
```

```
                45                    50
GTGAGCCCAT ATGTTTGTGT GCTCATGCCT GGGTTGTTGT GTCTGAGCCT GTCTTGGGTC      320

TGGGTGTTGG                                                              330
```

(2) INFORMATION FOR SEQ ID NO:10:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:10:

```
Ser Trp Ala Asn Lys Met Glu Ala Leu Thr Ser Lys Ser Ala Ala Asp
 1               5                  10                  15

Ala Glu Gly Tyr Leu Ala His Pro Val Asn Ala Tyr Lys Leu Val Lys
            20                  25                  30

Arg Leu Asn Thr Asp Trp Pro Ala Leu Glu Asp Leu Val Leu Gln Asp
        35                  40                  45

Ser Ala Ala
    50
```

(2) INFORMATION FOR SEQ ID NO:11:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 92...232
        (D) OTHER INFORMATION:

(xi) SEQUENCE DESCRIPTION: SEQ ID NO:11:

```
GAGACCCTCT TGTGGCTGC CTCTCTGGGT CCCAAGTGGA ATTCTGCCCC TGGATCAAGG         60

GTAATCTCTT GTTCTGACTC TTCATTTGGA A GGT TTT ATC GCC AAC CTC TCT         112
                                  Gly Phe Ile Ala Asn Leu Ser
                                   1               5

GTG CAG CGG CAG TTC TTC CCC ACT GAT GAG GAC GAG ATA GGA GCT GCC        160
Val Gln Arg Gln Phe Phe Pro Thr Asp Glu Asp Glu Ile Gly Ala Ala
         10                  15                  20

AAA GCC CTG ATG AGA CTT CAG GAC ACA TAC AGG CTG GAC CCA GGC ACA        208
Lys Ala Leu Met Arg Leu Gln Asp Thr Tyr Arg Leu Asp Pro Gly Thr
     25                  30                  35

ATT TCC AGA GGG GAA CTT CCA GGT AACTCACCAC TCCAGGCGTT GCTGTCCCGC       262
Ile Ser Arg Gly Glu Leu Pro Gly
40                  45

ATGTGTCTCT TTAGTGGCGG GACAGGTTGG AGCCACCACC AACTTGTGGC CTTTAACCTC      322

GGGTGCACCT CTCTCTTGGC ACACCAGTTG TGCTGGACTC CTCTCCA                    369
```

(2) INFORMATION FOR SEQ ID NO:12:

(i) SEQUENCE CHARACTERISTICS:
        (A) LENGTH: 47 amino acids
        (B) TYPE: amino acid
        (C) STRANDEDNESS: single
        (D) TOPOLOGY: linear -continued (ii) MOLECULE TYPE: protein (v) FRAGMENT TYPE: internal (xi) SEQUENCE DESCRIPTION: SEQ ID NO:12:

```
Gly Phe Ile Ala Asn Leu Ser Val Gln Arg Gln Phe Phe Pro Thr Asp
 1               5                  10                  15

Glu Asp Glu Ile Gly Ala Ala Lys Ala Leu Met Arg Leu Gln Asp Thr
                20                  25                  30

Tyr Arg Leu Asp Pro Gly Thr Ile Ser Arg Gly Glu Leu Pro Gly
            35                  40                  45
```

(2) INFORMATION FOR SEQ ID NO:13:

(i) SEQUENCE CHARACTERISTICS:
      (A) LENGTH: 309 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 3...239
      (D) OTHER INFORMATION:

(xi) SEQUENCE DESCRIPTION: SEQ ID NO:13:

```
GA ACC AAG TAC CAG GCA ATG CTG AGT GTG GAT GAC TGC TTT GGG ATG         47
   Thr Lys Tyr Gln Ala Met Leu Ser Val Asp Asp Cys Phe Gly Met
   1               5                  10                  15

GGC CGC TCG GCC TAC AAT GAA GGG GAC TAT TAT CAT ACG GTG TTG TGG        95
Gly Arg Ser Ala Tyr Asn Glu Gly Asp Tyr Tyr His Thr Val Leu Trp
                20                  25                  30

ATG GAG CAG GTG CTA AAG CAG CTT GAT GCC GGG GAG GAG GCC ACC ACA       143
Met Glu Gln Val Leu Lys Gln Leu Asp Ala Gly Glu Glu Ala Thr Thr
                35                  40                  45

ACC AAG TCA CAG GTG CTG GAC TAC CTA CGC TAT GCT GTC TTC CAG TTG       191
Thr Lys Ser Gln Val Leu Asp Tyr Leu Arg Tyr Ala Val Phe Gln Leu
            50                  55                  60

GGT GAT CTG CAC CGT GCC CTG GAG CTC ACC CGC CGC CTG CTC TCC CTT G     240
Gly Asp Leu His Arg Ala Leu Glu Leu Thr Arg Arg Leu Leu Ser Leu
        65                  70                  75

GTAAGGAGAT TCTAGGGGAA GGTAAGATGG GAATGGAGAG TGGCAGAGGA ACTGCACTGT     300

GCCTGGCAC                                                             309
```

(2) INFORMATION FOR SEQ ID NO:14:

(i) SEQUENCE CHARACTERISTICS:
      (A) LENGTH: 79 amino acids
      (B) TYPE: amino acid
      (C) STRANDEDNESS: single
      (D) TOPOLOGY: linear (ii) MOLECULE TYPE: protein (v) FRAGMENT TYPE: internal (xi) SEQUENCE DESCRIPTION: SEQ ID NO:14:

```
Thr Lys Tyr Gln Ala Met Leu Ser Val Asp Asp Cys Phe Gly Met Gly
 1               5                  10                  15

Arg Ser Ala Tyr Asn Glu Gly Asp Tyr Tyr His Thr Val Leu Trp Met
                20                  25                  30

Glu Gln Val Leu Lys Gln Leu Asp Ala Gly Glu Glu Ala Thr Thr Thr
                35                  40                  45

Lys Ser Gln Val Leu Asp Tyr Leu Arg Tyr Ala Val Phe Gln Leu Gly
```

```
                  50                  55                  60
Asp Leu His Arg Ala Leu Glu Leu Thr Arg Arg Leu Leu Ser Leu
65                  70                  75
```

(2) INFORMATION FOR SEQ ID NO:15:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 198...392
        (D) OTHER INFORMATION:

(xi) SEQUENCE DESCRIPTION: SEQ ID NO:15:

```
TTAGATGCTG TGAAGGATGA TGCACGCATG CAGGTGAGCT GCTGGGAGAG AAACCCTTAC     60

TACTCTGGTT AGATGCTGTG AAGGATGAAT GCAGCATGCA GGTGAGCTGC TCCCAGAGAA    120

ACCCTTACAG ATAATTTCTC TAAATGACCT AACAGATGTT GTGGTTTCC TTTTCCTTCT     180

CATTCCTTGC ATTTTCT GAC CCA AGC CAC GAA CGA GCT GGA GGG AAT CTG       230
                    Asp Pro Ser His Glu Arg Ala Gly Gly Asn Leu
                     1               5                   10

CGG TAC TTT GAG CAG TTA TTG GAG GAA GAG AGA GAA AAA ACG TTA ACA      278
Arg Tyr Phe Glu Gln Leu Leu Glu Glu Glu Arg Glu Lys Thr Leu Thr
             15                  20                  25

AAT CAG ACA GAA GCT GAG CTA GCA ACC CCA GAA GGC ATC TAT GAG AGG      326
Asn Gln Thr Glu Ala Glu Leu Ala Thr Pro Glu Gly Ile Tyr Glu Arg
         30                  35                  40

CCT GTG GAC TAC CTG CCT GAG AGG GAT GTT TAC GAG AGC CTC TGT CGT      374
Pro Val Asp Tyr Leu Pro Glu Arg Asp Val Tyr Glu Ser Leu Cys Arg
     45                  50                  55

GGG GAG GGT GTC AAA CTG GTGAGATGTG TGAGGGGGCT AGGGTGCCAA AGCTGTGG    430
Gly Glu Gly Val Lys Leu
60                  65

ACCTGGACTC TGGCCTCTGG GCAGGCAGAT TTGGGGAAGG TGTTCTTTAT TCTGAGGTAC    490

TTTTCACGTT TCCCGTTTT                                                  509
```

(2) INFORMATION FOR SEQ ID NO:16:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:16:

```
Asp Pro Ser His Glu Arg Ala Gly Gly Asn Leu Arg Tyr Phe Glu Gln
1               5                   10                  15

Leu Leu Glu Glu Glu Arg Glu Lys Thr Leu Thr Asn Gln Thr Glu Ala
             20                  25                  30

Glu Leu Ala Thr Pro Glu Gly Ile Tyr Glu Arg Pro Val Asp Tyr Leu
         35                  40                  45

Pro Glu Arg Asp Val Tyr Glu Ser Leu Cys Arg Gly Glu Gly Val Lys
     50                  55                  60

Leu
65
```

(2) INFORMATION FOR SEQ ID NO:17:

(i) SEQUENCE CHARACTERISTICS:
        (A) LENGTH: 2121 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 96...272
        (D) OTHER INFORMATION:

(xi) SEQUENCE DESCRIPTION: SEQ ID NO:17:

```
TGGCCATGAG GTGAGTCCAG TGTCTGCAGA CAGCCAGACT GGGACCGAGG ATTAGGACTC      60

ACTCAGCTCA GGGCCTGTTA CTCTGTGCTT TCCAG ACA CCC CGT AGA CAG AAG        113
                                       Thr Pro Arg Arg Gln Lys
                                         1               5

AGG CTT TTC TGT AGG TAC CAC CAT GGC AAC AGG GCC CCA CAG CTG CTC       161
Arg Leu Phe Cys Arg Tyr His His Gly Asn Arg Ala Pro Gln Leu Leu
         10                  15                  20

ATT GCC CCC TTC AAA GAG GAG GAC GAG TGG GAC AGC CCG CAC ATC GTC       209
Ile Ala Pro Phe Lys Glu Glu Asp Glu Trp Asp Ser Pro His Ile Val
             25                  30                  35

AGG TAC TAC GAT GTC ATG TCT GAT GAG GAA ATC GAG AGG ATC AAG GAG       257
Arg Tyr Tyr Asp Val Met Ser Asp Glu Glu Ile Glu Arg Ile Lys Glu
     40                  45                  50

ATC GCA AAA CCT AAA GTAGGTGTAC AGTGAGGCCT TCTCGGGTCA CTGAAGGGGG A     313
Ile Ala Lys Pro Lys
55

AGGTCTTTTT CTCATCCCCT AGCACTATGG GTGGTTAGAG TTTGCCCATC CTAGCCACCC    373

TTTATCCATA TCTAGCATAG GGCCTACCTG GAGGGATACA GAGATGCTTC AGACTCAGCC    433

TGACCTTGTG AGGTTCATGT GCCAGTGGAA GGAAGGAACA GGGTAACCAA TGTGGACAGC    493

CAAGTGCTAT CATACAAGGT CACGTCCTGG AACAGGGCT GGGAACAGGG CAGGTCTACA     553

CTGGTGTGTC AGTTCACCTG GTTGGGAGAC TGGTGCGTGG GTGAGTTTTT TGGAAATGTT    613

CCATAGGATG CTATGAAGCT GGGTCCTGTG GAGCTCCTGA GTAGGACTGT AAATGAGGTG    673

AATGACTTAG AGGAGAATGT ATATCTTTTA TAATATTTGG GTCTCTCATC CAAGGGCATG    733

ACAGGTCTCT CCATATCTTT TTAAGTTTTC TTCATATAAG CCTTGAACAT GTCTTAAGTT    793

TATTCCTTGG TACTTTCTTT GTTACTGTTA ATTTACTTTA TTTCTTCATT ATTATTTTAA    853

CTGGTTACAT TATTTATTAG TTTACTATTA TATGCCAAAC TATTGATTTT ACAAATACAT    913

TTCATAGTAA GAGCTAATGT TTACTGAATT CTTAACTGTG GCAGGAAACT TCTAAGTGCT    973

TAACATATAT ATTAAGTGTT ATGTCACAGT TATGAACAGC TGCTCAGAAT GATGTCACTG   1033

TCTCTGTTTT ACCTATGAAA AAGCAAACTC ATACAGATTG CAGCTAGTGG TTGAATTTAC   1093

TTATTTGTTT TTTGGTTTTA CGTGATTTCT CTTTGGTTGG GTGGATAGCA TTAACACCTG   1153

GAAATAAGGA AAATTTTATT TTCTCCTGAT ACTTGTAGTT CCTTTGTTTT TATAACCTTA   1213

TTGAATTGCC CAGAACTTCT AGAGCATAAT TACGTAGAAT AGGCATCCTT GTCTCATTCC   1273

TGAATTTCCT GGGAAATTCC TATGGTATTT ACTGCTAAGA ATGCAGTTGG CTGTTGGTTT   1333

TGTATATATG CCAAAATTAT TCTTCTGTTT CTAGTTCATA AAAGATTTGT TCCCCATTTG   1393

ACATCTTTCA AAGAGACCTA TTTGCTGCCA TATCCCATCA CTGATGATTG GGAGGGAGGA   1453

TTTAGCTCGA TTCTCTATGC TCTGCTCCTA ATAGAATTGT AGGGGCCGAG GTGACCAGGA   1513

GGCCCGACAC TCATGGAGAG ACCTGAAATA GGTTCCTATC CTGGCCCCTG GACCTCATCT   1573
```

```
TGGAACAGCT TTGGCTTGAG GTACTAGGAC ATCTAGGGCT TTGAGTCAGT GGTTGGCATC    1633

ATCGATGTGG CTGAGGAAGG GGGCTAGCCA GATATATGGA GAATGGGGAC TAGGACTCCC    1693

CTTTCTACTC AGCTCCAGAG TCCTCCAGGA AAGAAAACTA CTTTGTTGGT TGTGCCAGGT    1753

TTCCTGAGAG ATTCCTTACC CGTTCTTTCA GTTCCAGACA CTGAGAACAT TTCTCTGTGC    1813

ATGTGTGCAT ATGTGTACAC ATGTGTGTGG CTGGCCACAG GGTAGTGTTA GGAAAAGATA    1873

TATTTGAATA GAAGCCATGC AAAGAGCCAA ACAAGGTTGG CAAACATGTT TGGCTCTTAA    1933

CATGGCTTCT ATTCAAAGAT AAGCTGACCC CTCCTTTCCG GAGACTGTGA GGGACAGATG    1993

CTATTCTGGC TTTCAAGTAG AGCCAATGAG CTTAACTTGG CCTGTGGGGA ATGCCTGGCA    2053

GCTGTCTGTG GGGGCTCTTG GCCTGCTTTC AAAATAGCCC TGTCGTTAAA ATGGGACAGC    2113

ATCAGTGC                                                            2121
```

(2) INFORMATION FOR SEQ ID NO:18:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:18:

```
Thr Pro Arg Arg Gln Lys Arg Leu Phe Cys Arg Tyr His His Gly Asn
 1               5                  10                  15

Arg Ala Pro Gln Leu Leu Ile Ala Pro Phe Lys Glu Glu Asp Glu Trp
            20                  25                  30

Asp Ser Pro His Ile Val Arg Tyr Tyr Asp Val Met Ser Asp Glu Glu
        35                  40                  45

Ile Glu Arg Ile Lys Glu Ile Ala Lys Pro Lys
    50                  55
```

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:19:

```
AAGTTGCGGC CGCGAGCATC AGCAAGGTAC TGC                                 33
```

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:20:

```
TGTCCGGATC CAGTTTGTAC GTGTC                                          25
```